US008181647B2

(12) United States Patent
Ishizeki et al.

(10) Patent No.: US 8,181,647 B2

(45) Date of Patent: May 22, 2012

(54) POWDER MEDICINE ADMINISTERING DEVICE

(75) Inventors: Kazunori Ishizeki, Gunma (JP); Hisatomo Ohki, Gunma (JP); Shigemi Nakamura, Gunma (JP); Akira Yanagawa, Yokohama (JP)

(73) Assignees: Hitachi, Ltd., Tokyo (JP); Dott Limited Company, Kanagawa (JP)

( * ) Notice: Subject to any disclaimer, the term of this patent is extended or adjusted under 35 U.S.C. 154(b) by 1120 days.

(21) Appl. No.: 11/448,754

(22) Filed: Jun. 8, 2006

(65) Prior Publication Data

US 2006/0283445 A1 Dec. 21, 2006

(30) Foreign Application Priority Data

Jun. 8, 2005 (JP) ................................ 2005-168681
Mar. 8, 2006 (JP) ................................ 2006-062700

(51) Int. Cl.
*A61M 16/00* (2006.01)
*A61M 15/00* (2006.01)

(52) U.S. Cl. .......... 128/203.28; 128/203.14; 128/203.12

(58) Field of Classification Search ............. 128/200.24, 128/203.12, 203.15, 203.24, 207.18; 222/630, 222/637, 195, 505, 547, 559, 561; 221/263, 221/270, 257, 221, 301
See application file for complete search history.

(56) References Cited

U.S. PATENT DOCUMENTS 4,013,075 A 3/1977 Cocozza
5,161,524 A * 11/1992 Evans ...................... 128/203.15
5,201,308 A * 4/1993 Newhouse ............... 128/203.15
5,702,362 A * 12/1997 Herold et al. .................... 604/58
5,810,004 A * 9/1998 Ohki et al. ............... 128/203.15
6,575,160 B1 * 6/2003 Volgyesi .................. 128/203.15
7,540,282 B2 * 6/2009 O'Leary .................. 128/200.23
2002/0158150 A1 10/2002 Matsugi et al.
2002/0179086 A1 12/2002 Chang
2003/0183230 A1 10/2003 Nelson et al.
2004/0069303 A1 * 4/2004 Brown et al. ............ 128/203.15
2005/0103336 A1 * 5/2005 Nishibayashi et al. .. 128/203.11

FOREIGN PATENT DOCUMENTS

DE 4227731 A1 2/1994
JP 2003-175103 A 6/2003
WO 2004/060458 A 7/2004

OTHER PUBLICATIONS

European Office Action corresponding to European Patent Application No. 06010933.7, dated May 30, 2011.

* cited by examiner

*Primary Examiner* — Justine Yu
*Assistant Examiner* — Rachel Young
(74) *Attorney, Agent, or Firm* — Sughrue Mion, PLLC

(57) ABSTRACT

A powder medicine administering device includes a main body, an air supply section, and a movable member slidably attached to the main body, and arranged to be moved relative to the main body from a first position through a second position to a third position. One of the main body and the movable member includes a side wall portion defining a medicine storage chamber including an opening closed by a sliding surface of the other of the main body and the movable member at the second position of the movable member, and a medicine discharge passage. The other of the main body and the movable member is formed with a medicine carrying chamber connected with the opening of the medicine storage chamber at the first position of the movable member, and connected with the medicine discharge passage at the third position of the movable member.

16 Claims, 18 Drawing Sheets

POWDER MEDICINE ADMINISTERING DEVICE

BACKGROUND OF THE INVENTION

The present invention relates to a powder medicine administering device to administer a powder medicine.

Japanese Patent Application Publication No. 2003-175103 shows a powder medicine administering device including a substantially cylindrical medicine storage member formed with a medicine receiving chamber opened in a flat bottom surface of the medicine storage member, a medicine guiding member arranged to be rotated while abutting on the bottom surface of the medicine storage member, and an air passage. A powder medicine is guided from the medicine storage member Into the medicine receiving chamber. The medicine guiding member is rotated to level off the powder medicine, so that a dose of the powder medicine is measured. The medicine guiding member is further rotated to a position at which the medicine receiving chamber is connected with the air passage, and the powder medicine within the medicine receiving chamber is guided into the air passage. In this state, a pump is operated, and the air is supplied under pressure. Consequently, the powder medicine is discharged from a nozzle to the outside.

SUMMARY OF THE INVENTION

However, the above-mentioned powder medicine administering device has the flat bottom surface of the medicine storage member, and the medicine guiding member includes an outer surface located at a lower portion of the medicine storage member, and inclined downward toward an outer periphery. The powder medicine gathers in a periphery of the bottom portion of the medicine storage member which is out an opening of the medicine receiving chamber. Accordingly, it is difficult to introduce the powder medicine into the medicine receiving chamber opened in a portion of the bottom surface of the medicine storage member. Therefore, the powder medicine may be remained within the medicine storage member.

It is an object of the present invention to provide a powder medicine administering device devised to restrict the powder medicine from remaining within the powder medicine administering device.

According to one aspect of the present invention, a powder medicine administering device comprises: a main body; an air supply section arranged to supply air under pressure; and a movable member slidably attached to the main body, and arranged to be moved relative to the main body from a first position through a second position to a third position, one of the main body and the movable member including a side wall portion defining a medicine storage chamber receiving a powder medicine in a substantially closed state, and including an opening closed by a sliding surface of the other of the main body and the movable member when the movable member is located at the second position, the side wall portion being inclined radially inward toward the opening near the opening of the medicine storage chamber, the one of the main body and the movable member being formed with a medicine discharge passage arranged to receive the supply of the air from the air supply section and the other of the main body and the movable member being formed with a medicine carrying chamber arranged to be connected with the opening of the medicine storage chamber when the movable member is located at the first position, and arranged to be connected with the medicine discharge passage when the movable member is located at the third position.

BRIEF DESCRIPTION OF THE DRAWINGS

DETAILED DESCRIPTION OF THE INVENTION (First embodiment) FIG. 1 shows a side view showing a powder medicine administering device being in an administration disable state (administration inhibition state), and according to a first embodiment of the present invention. FIG. 2 shows a side view showing the powder medicine administering device of FIG. 1, being in an administration enable state (administration permission state). FIG. 3 shows a longitudinal sectional view showing the powder medicine administering device of FIG. 1, being in the administration disable state. FIG. 4 shows a longitudinal sectional view showing the powder medicine administering device of FIG. 2, being in the administration enable state. FIG. 5A shows a plan view (top view) showing a slider of the powder medicine administering device of FIG. 1, being in the administration disable state. FIG. 5B shows a plan view (top view) showing the slider of the powder medicine administering device of FIG. 2, being in the administration enable state. FIG. 6A shows a cross sectional view taken along a section line VIA-VIA of FIG. 3, showing a main body of the powder medicine administering device of FIG. 1. FIG. 6B shows a longitudinal sectional view taken along a section line VIB-VIB of FIG. 6A. FIG. 7 shows a longitudinal sectional view taken along a section line VII-VII of FIG. 6A. FIG. 8A shows a longitudinal sectional view showing a stirred flow forming section of the powder medicine administering device of FIG. 1. FIG. 8B shows a cross sectional view taken along a section line VIIIB-VIIIB of FIG. 8A.

As shown in FIGS. 1~4, powder medicine administering device 1 includes a main body 2, a nozzle portion 4, a pump member 5, a slider 7, and an air induction member 12. Body member 2 is formed with a medicine storage chamber 3 for storing a powder medicine. Nozzle portion 4 serves as an outlet nozzle for powder medicine discharge passages. Pump member 5 serves as an air supply mechanism or section arranged to supply the air to the medicine discharge passage formed in main body 2, for discharging the powder medicine. Slider 7 serves as a movable member slidably (rotatably) supported on main body 2. Air induction member 12 introduces the air into pump member 5.

Figure 1:
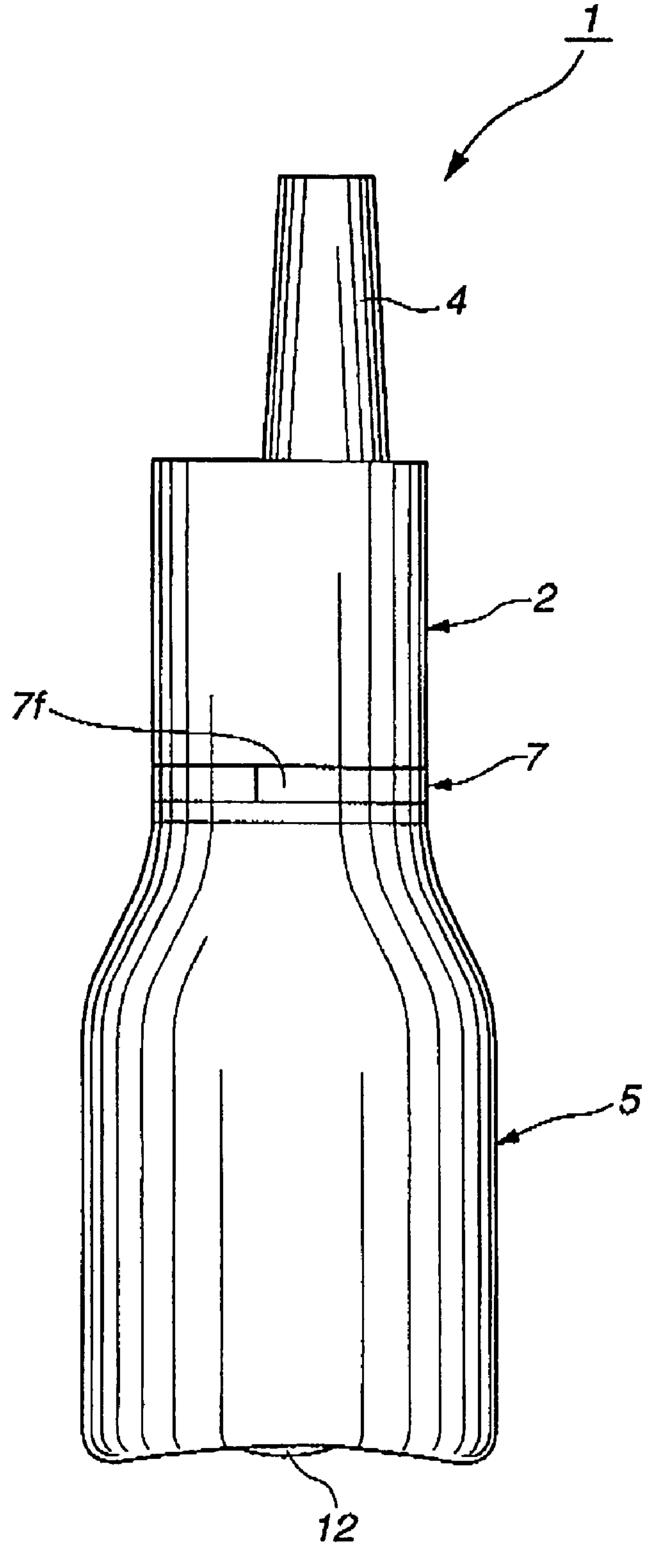
FIG. 1 is a side view showing a powder medicine administering device being in an administration disable state, according to a first embodiment of the present invention.
Figure 2:
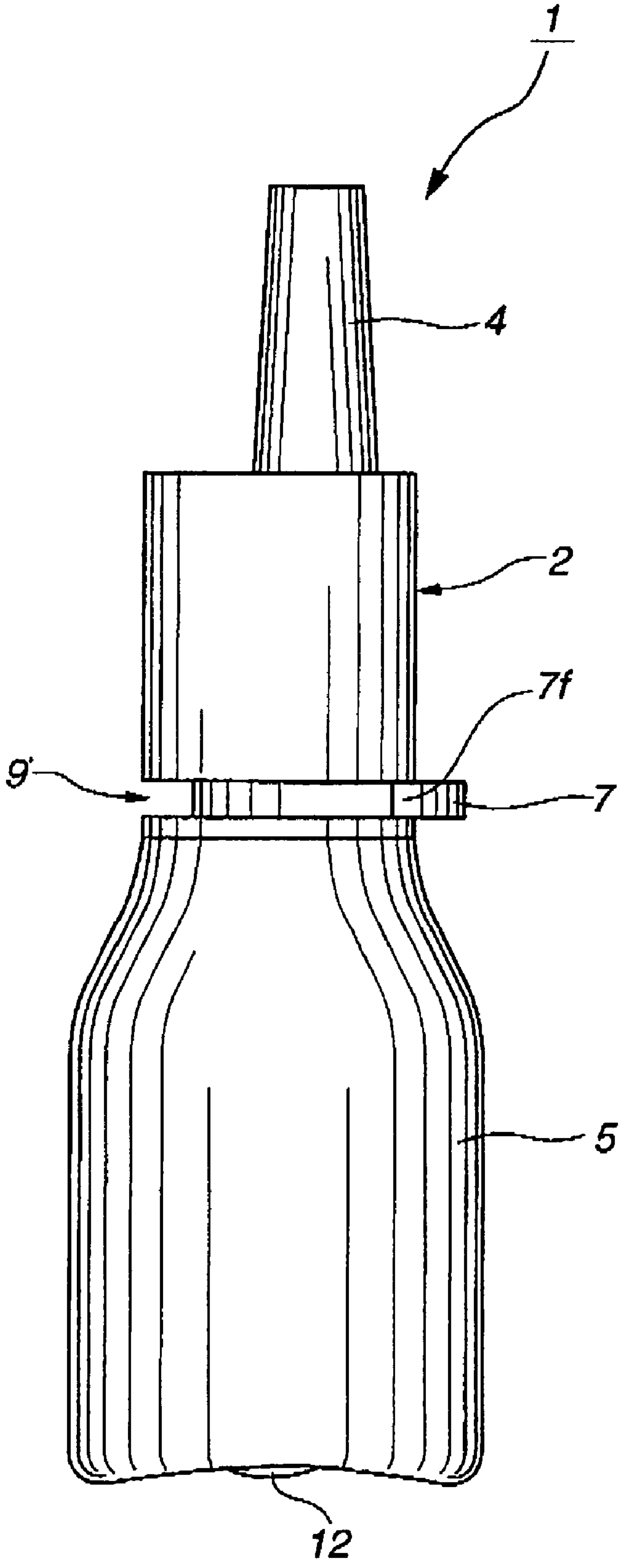
FIG. 2 is a side view showing the powder medicine administering device of FIG. 1, being in an administration, enable state.

Powder medicine administering device 1 is shaped like a body of revolution having an axis extending in an up-down direction of FIG. 1, except for slider 7. Powder medicine administering device 1 includes pump member 5 having a lower portion having a diameter larger than a diameter of an upper portion, and thereby can be disposed in a posture in which pump member 5 is positioned below, and in which nozzle portion 4 is positioned above. Besides, it is optional to write that powder medicine administering device 1 is urged to be disposed in that posture at the time of nonuse, in an outside surfaces a manual, and so on. At the time of use, powder medicine administering device 1 is used in the same posture because nozzle portion 4 is inserted into nasal cavity.

Medicine storage chamber 3 is formed within main body 2 as a closed space isolated from outside air in a substantially airtight state (closed state). Medicine storage chamber 3 includes an opening 2*q* located on a slider 7's side, and closed by an upper surface 7*d* of slider 7. Main body 2 includes a cylindrical portion 2*p* extending in the up-down direction of FIG. 1, and defining medicine discharge passages 20 (2*f*, 2*g* and 2*h*) as a space within the cylinder.

Slider 7 is formed with a recessed portion 7*c* serving as a medicine carrying chamber 8. At the time of the nonuse (in the administration disable state), medicine carrying chamber 8 is connected with opening 2*q* formed in a bottom portion of medicine storage chamber 3. Slider 7 is slidably attached to main body 2 in a direction crossing the axial direction of powder medicine administering device 1 (in a direction perpendicular to the axial direction of powder medicine administering device 1 in the first embodiment). Slider 7 is slid (moved), and medicine carrying chamber 8 is slid, through a position at which medicine carrying chamber 8 is closed by an upper surface 9*a* and a lower surface 9*b* of a gap 9 (sliding surfaces of main body 2 with slider 7), to a position to confront (be connected with) medicine discharge passage 20 (2*f*). Consequently, a powder medicine 30 within medicine carrying chamber 8 is introduced into medicine discharge passage 20 (in the administration enable state). Powder medicine administering device 1 includes a lock mechanism (not shown) arranged to lock slider 7 to main body 2 by fitting between a projection and a recessed portion, in the administration enable state and/or the administration disable state. In the device according to the first embodiment of the present invention, upper surface 9*a* of gap 9 serves as a level surface for powder medicine 30, and powder medicine 30 of volume of medicine carrying chamber 8 is transferred. That is, a dose of the powder medicine is provided (measured) as the volume of medicine carrying chamber 8.

Figure 4:
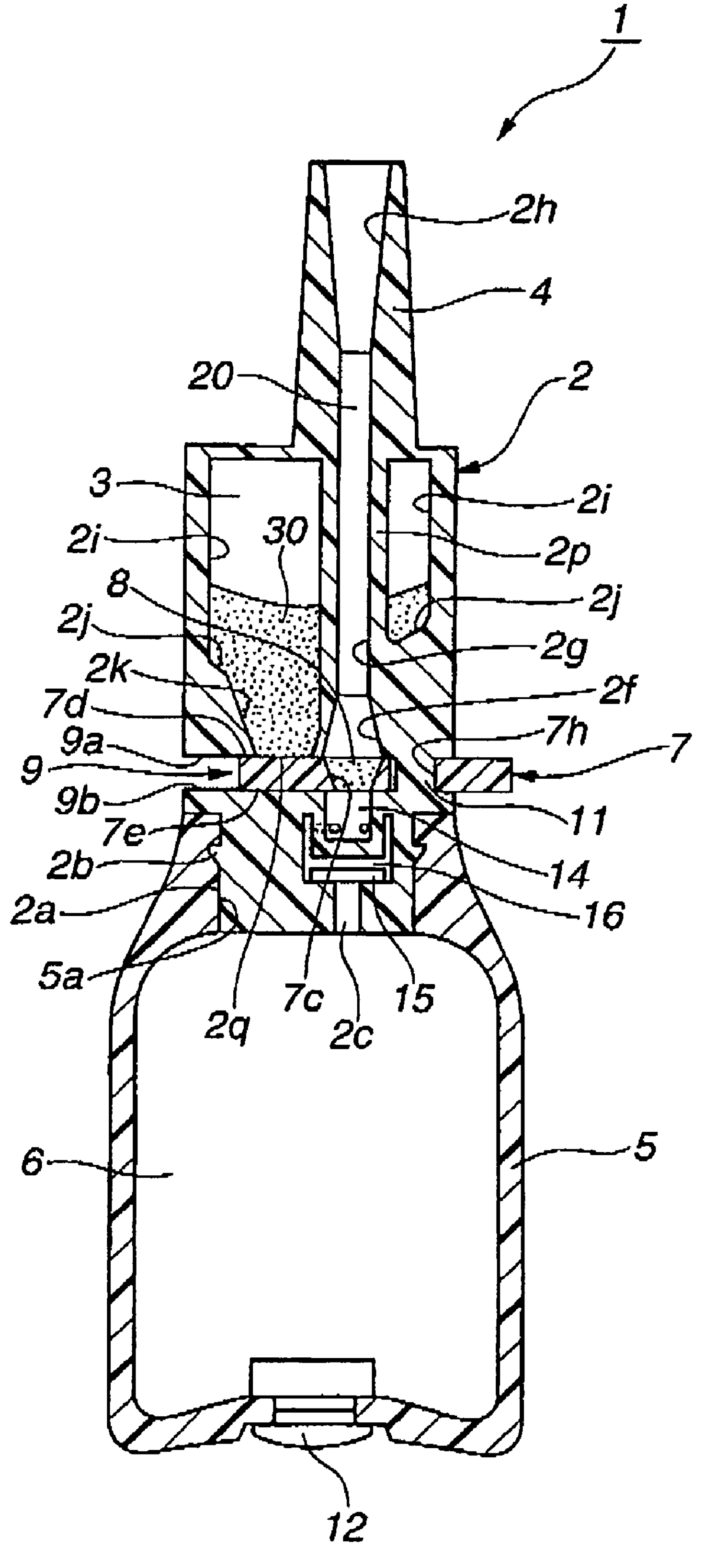
FIG. 4 is a longitudinal sectional view showing the powder medicine administering device of FIG. 2, being in the administration enable state.

In the administration enable state as shown in FIG. 4, medicine carrying chamber 8 is connected with a lower end of an inner cylindrical portion 2*f* formed in main body 2. An upstream portion (lower portion in the posture at the time of the use) of medicine carrying chamber 8 is connected with a cylindrical stirred flow forming chamber 14. That is, in the posture of powder medicine administering device 1 at the time of the use, the powder medicine is transferred to the connection position with inner cylindrical portion 2*f* by medicine carrying chamber 8 as described above, and guided into stirred flow forming chamber 14 by (under) the force of the gravity. Stirred flow forming chamber 14 serves as a medicine receiving chamber for receiving the powder medicine because stirred flow forming chamber 14 has the cylindrical shape with a bottom portion. The air supplied under the pressure is introduced into stirred flow forming chamber 14, so that the swirl flow (rotating flow) is formed. The powder medicine is curled up by the swirl flow so that the air and the power medicine are stirred. Therefore, it is possible to restrict the powder medicine from remaining in medicine discharge passage 20, and to discharge the powder medicine in a more diffuse state.

The air and the powder medicine are sufficiently stirred in stirred flow forming chamber 14. The mixed flow of the air and the powder medicine is introduced to medicine discharge passage 20, and discharged from a nozzle hole (an inner cylindrical portion 2*h*) of nozzle portion 4 to the outside in the more diffuse state. Accordingly, it is possible readily to lead the powder medicine to mucous membrane of bottom of the nasal cavity because nozzle portion 4 is used in a state to be inserted into the nasal cavity.

Slider 7 is a substantially circular plate member with a uniform thickness. Slider 7 is fit in circular gap 9 formed in a substantially central portion of main body 2 in the axial direction of main body 2. In this example, slider 7 is sandwiched (interposed) between upper surface 9*a* and lower surface 9*b* of gap 9, by appropriate pressing force. Main body 2 and slider 7 are made from resin material having elasticity. The surfaces abutted on each other (upper surface 9*a* of gap 9 and upper surface 7*d* of slider 7, lower surface 9*b* of gap 9 and lower surface 7*b* of slider 7) have appropriate surface roughness. Accordingly, it is possible to ensure the air tightness between the abutment surfaces, and to restrict leakage of the powder medicine. By the above-described sealing arrangement, it is possible to store powder medicine 30 within medicine storage chamber 3 in a state to ensure the air tightness against the outside, and to restrict powder medicine 30 from deteriorating by oxidation and absorbability.

Figure 3:
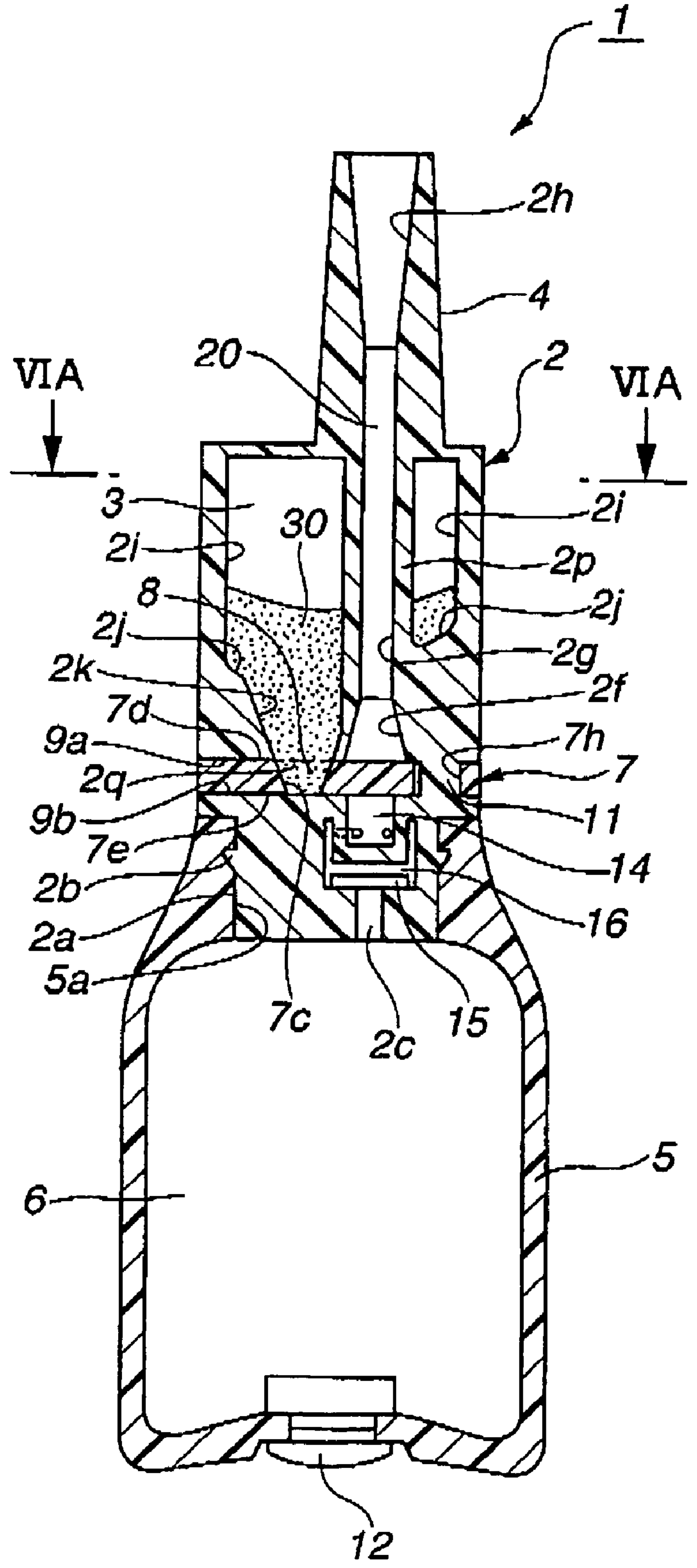
FIG. 3 is a longitudinal sectional view showing the powder medicine administering device of FIG. 1, being in the administration disable state.
Figure 5A:
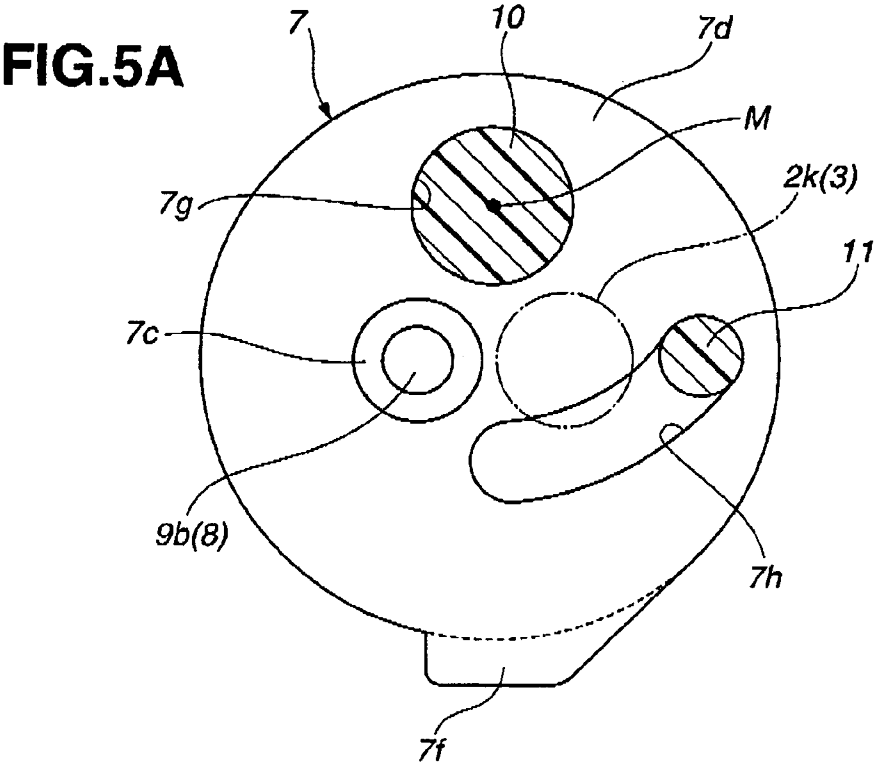
FIG. 5A is a plan view showing a slider of the powder medicine administering device of FIG. 1, being in the administration disable state.
Figure 5B:
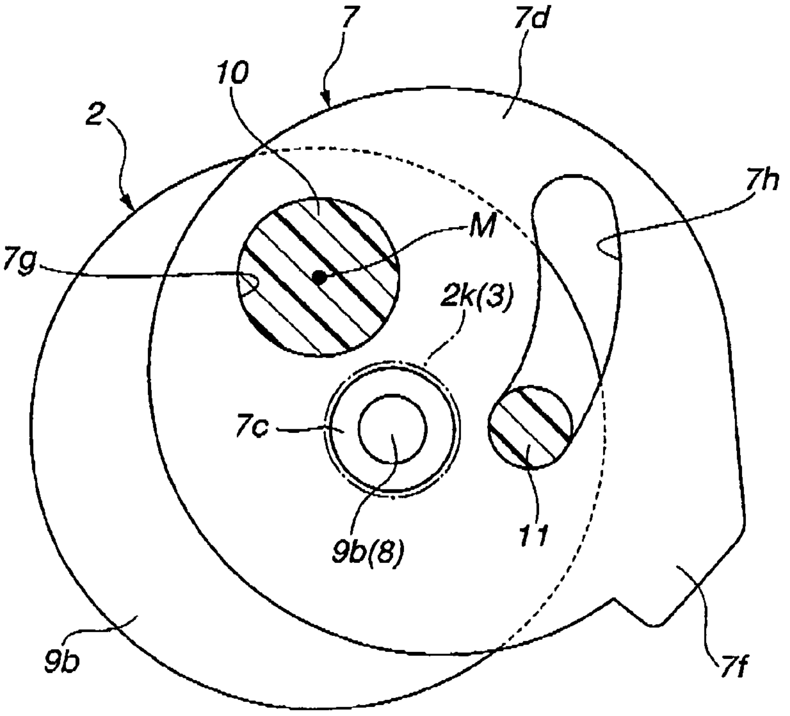
FIG. 5B is a plan view showing the slider of the powder medicine administering device of FIG. 2, being in the administration enable state.
Figure 6A:
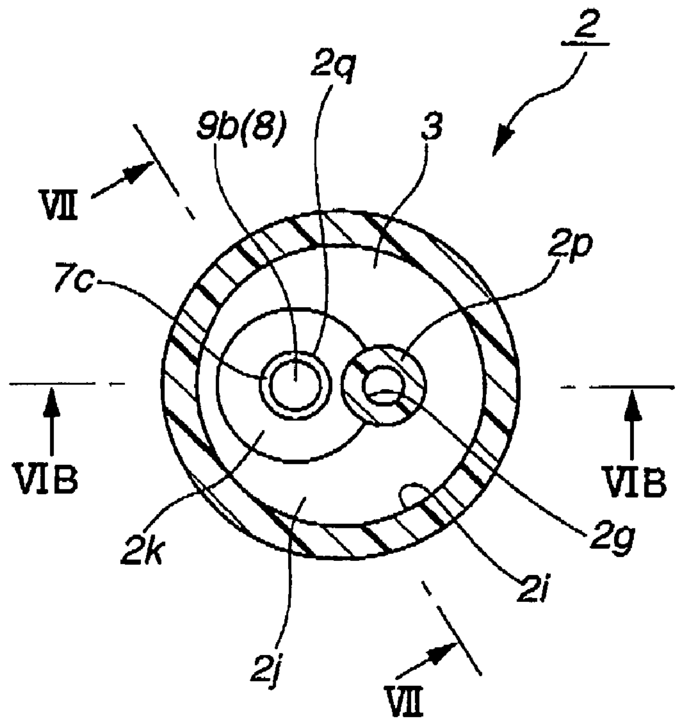
FIG. 6A is a cross sectional view taken along a section line VIA-VIA of FIG. 3, showing a main body of the powder medicine administering device of FIG. 1.
Figure 6B:
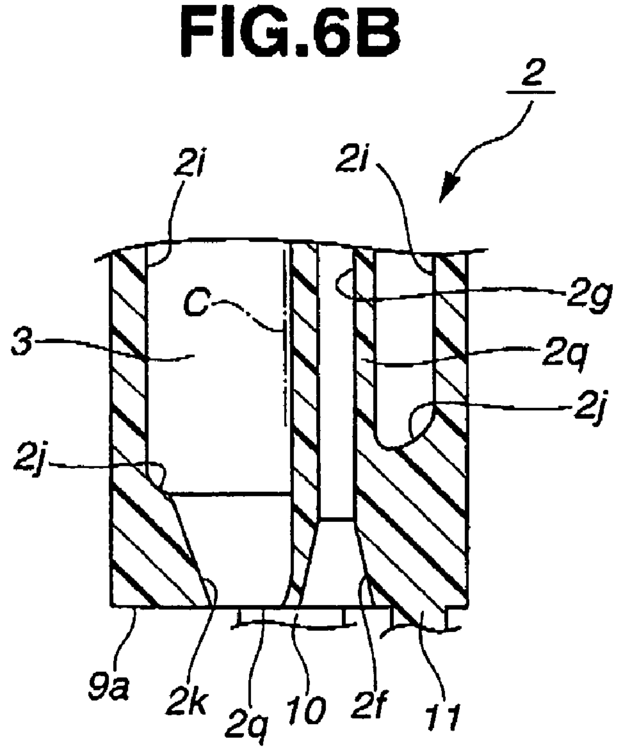
FIG. 6B is a longitudinal sectional view taken along a section line VIB-VIB of FIG. 6A.
Figure 7:
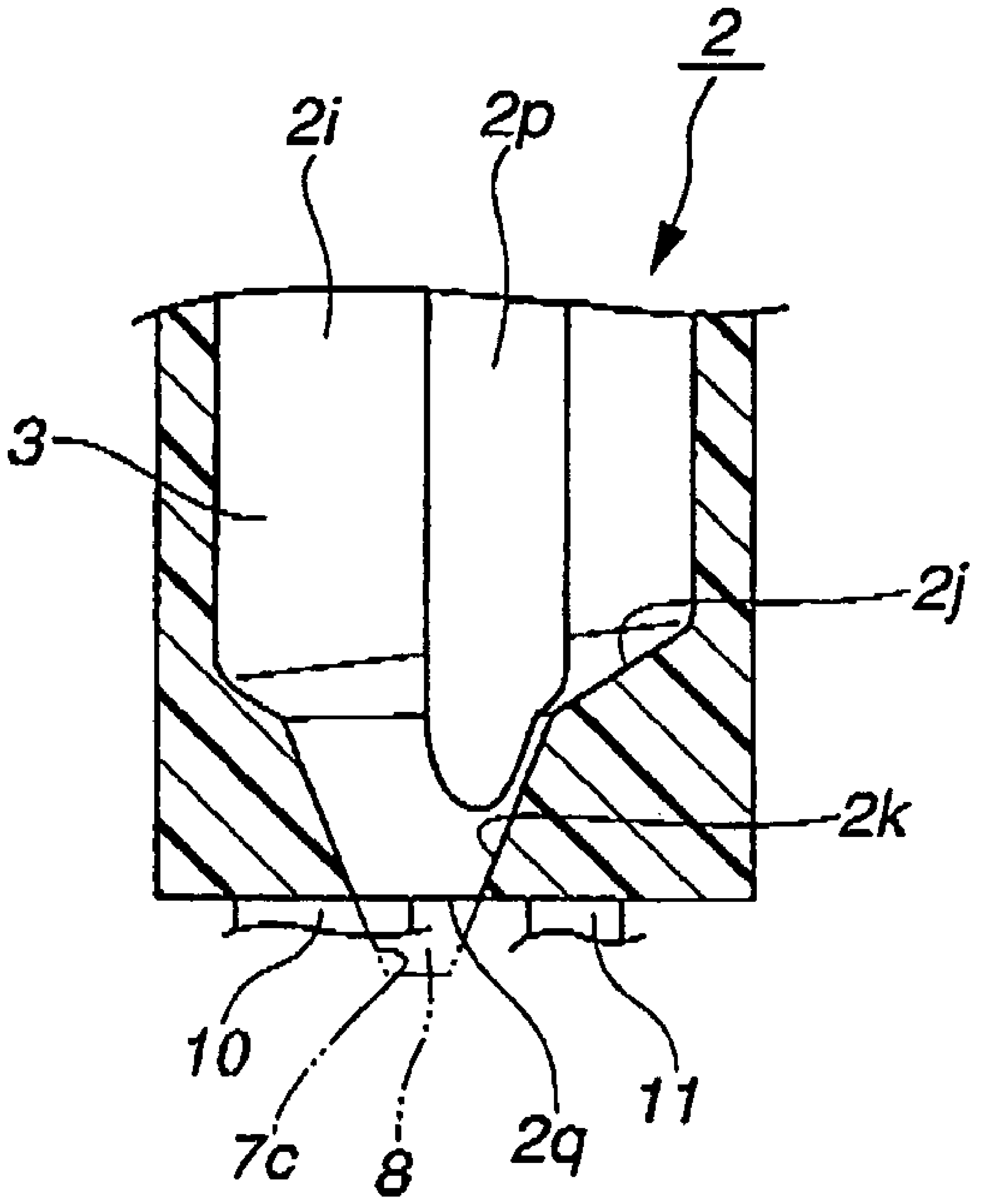
FIG. 7 is a longitudinal sectional view taken along a section line VII-VII of FIG. 6A, and showing the main body of the powder medicine administering device.

As shown in FIGS. 5A and 5B, main body 2 is formed with a cylindrical bridge portion 10 extending within gap 9 in the axial direction (in the up-down direction in FIG. 3). Slider 7 is formed with a through hole 7*g*. Bridge portion 10 of main body 2 is inserted into through hole 7*g* of slider 7, and slider 7 is arranged to be rotated (pivoted) about a center M of bridge portion 10. Bridge portion 10 is appropriately separated from the center axis of powder medicine administering device 1. Accordingly, an operating portion 7*f* projecting outwards is pushed by the finger, and slider 7 is moved along the outer surface of powder medicine administrating device 1, in a right direction of FIG. 5A. Slider 7 is pivoted in a counter-clock direction, and projected sidewards.

In the device according to the first embodiment of the present invention, slider 7 is received in the administration disable state, and projected outwards from the outer surface of powder medicine administering device 1 (outer surface of main body 2) in the administration enable state. Accordingly, the user can judge whether powder medicine administering device 1 is in the administration enable state or in the administration disable state, by the change in the external appearance. Moreover, it is possible to prompt the user to return to the administration disable state by the operation to restore the outwards projecting portion of slider 7.

Moreover, main body 2 includes a cylindrical bridge portion 11 in addition to bridge portion 10. Slider 7 is formed with a through long hole 7*h* shaped like an arc with center M. Bridge portion 11 is loosely inserted into through long hole 7*h*, and slider 7 is moved along through long hole 7*h*. That is, operating positions of slider 7 in the administration enable state or in the administration disable state and an amount of the projection of slider 7 in the administration enable state are determined by position between bridge portion 11 and through long hole 7*h*.

Slider 7 includes recessed portion 7*c* serving as medicine carrying chamber 8. Recessed portion 7*c* extends from an upper surface 7*d* to a lower surface 7*e*. Recessed portion 7*c* is in a V-shaped form or tapered form Recessed portion 7*c* has a larger diameter at upper surface 7*d* than a diameter at lower surface 7*c*. The diameter of recessed portion 7*c* is gradually decreased from upper surface 7*d* to lower surface 7*c*. When powder medicine administering device 1 is in the administration disable state in which slider 7 is not slid (as shown FIG. 3), recessed portion 7*c* is aligned with an inner cylindrical portion 2*k* of medicine storage chamber 3. Recessed portion 7*c* is connected with opening 2*q* of medicine storage chamber 3, and serves as a bottom portion of medicine storage chamber 3. When powder medicine administering device 1 is in the administration enable state in which slider 7 is slid (as shown in FIG. 4), recessed portion 7*c* is aligned with inner cylindrical portion 2*f* of medicine discharge passage 20 so that a side wall surface (inner surface) of inner cylindrical portion 2*k* is smoothly connected with a side wall surface (inner surface) of recessed portion 7*c*. By this arrangement, powder medicine 30 is gathered into medicine carrying chamber 8 (the bottom portion of medicine storage chamber 3) by the force of the gravity, and medicine carrying chamber 8 is moved to medicine discharge passage 20 to define the predetermined amount of the powder medicine. Accordingly, it is possible to introduce powder medicine 30 within medicine storage chamber 3, through medicine carrying chamber 8 serving as the bottom portion, to medicine discharge passage 20, without leaving powder medicine 30 in medicine storage chamber 3. It is possible to restrict the powder medicine from remaining in the medicine storage chamber, relative to the above-mentioned conventional device which the powder medicine is introduced into the medicine discharge passage (the medicine receiving portion) by operation of the movable medicine introduction member provided on the flat bottom surface of the medicine storage chamber.

Medicine storage chamber 3 includes an inner cylindrical portion or side wall portion 2*i*, an inner cylindrical portion or side wall portion 2*j*, and inner cylindrical portion or side wall portion 2*k* which have inclinations different from each other. Inner cylindrical portion 2*i* is located at a highest position. Inner cylindrical portion 2*k* is located at a lowest position. Inner cylindrical portion 2*j* is located between inner cylindrical portion 2*i* and inner cylindrical portion 2*k*. Inner cylindrical portion 2*i* has a circular section with a uniform diameter. Inner cylindrical portion 2*i* has a side wall surface extending in the axial direction (the up-down direction in FIG. 3), and being curved in the circumferential direction. Inner cylindrical portions 2*k* and 2*j* located below inner cylindrical portion 2*i* are inclined radially inward toward opening 2*q*. A diameter of inner cylindrical portions 2*j* is gradually decreased from an upper surface to a lower surface. A diameter of inner cylindrical portions 2*k* is gradually decreased from an upper surface to a lower surface. Each of inner cylindrical portions 2*j* and 2*k* is in the form of V-shape. Inner cylindrical portion 2*k* has a gradient steeper (larger) than a gradient of inner cylindrical portion 2*j*. By this arrangement, it is possible to change the falling direction in the middle of the falling of powder medicine 30 when powder medicine 30 is dropped to the bottom portion. The powder medicine used in powder medicine administering device 1 may be concentrated in the medicine storage chamber to form bridges between the side wall surfaces confronting each other. However, in the device according to the first embodiment of the present invention, it is possible to vary the movement of powder medicine 30 within medicine storage chamber 3, and to uniformize voids between the particles. Accordingly, it is possible to restrict powder medicine 30 from concentrating and adhering in medicine storage chamber 3, without detracting from fluidity, and to certainly fill the predetermined amount of powder medicine 30 by medicine storage chamber 3.

In the device according to the first embodiment, in the administration disable state, medicine carrying chamber 8 (recessed portion 7*c*) is smoothly connected with inner cylindrical portion 2*k* of medicine storage chamber 3, and recessed portion 7*c* and inner cylindrical portion 2*k* form continuous side surface which does not have stepped portions. Accordingly, powder medicine 30 is smoothly guided from upper portion of medicine storage chamber 3 to medicine carrying chamber 8 serving as the bottom portion of medicine storage chamber 3.

In the administration disable state as shown in FIGS. 3 and 5A, medicine carrying chamber 8 (serving as the bottom portion of medicine storage chamber 3) is located at a position which is off (eccentric to) a center C of the upper portion of medicine storage chamber 3. By this arrangement, powder medicine 30 located on a left side (in FIGS. 3 and 4) of center of medicine storage chamber 3 is moved to medicine carrying chamber 8 by the way of substantially straight line. Powder medicine 30 located on a right side (in FIGS. 3 and 4) of center of medicine storage chamber 3 is moved obliquely downward to medicine carrying chamber 8. In this way, the gradients (inclinations) of the side wall surface of medicine storage chamber 3 are varied in accordance with positions, and the bottom portion (medicine carrying chamber 8) is located at a position eccentric to center C of the upper portion of medicine storage chamber 3, so that the falling directions of the powder medicine on the right and left sides of center of medicine storage chamber 3 are different from each other. Accordingly, it is possible to uniformize the voids between the particles, without decreasing the fluidity, to restrict powder medicine 30 from concentrating and adhering in medicine storage chamber 3, and to certainly fill the predetermined amount of powder medicine 30 by medicine storage chamber 3.

At a substantially central portion of medicine storage chamber 3, there is provided cylindrical portion 2*p* extending in the axial direction, and defining medicine discharge passage 20. Powder medicine 30 located on an opposite side of cylindrical portion 2*p* with respect to medicine carrying chamber 8 falls and rotates around the circumference of cylindrical portion 2*p* within medicine storage chamber 3. Accordingly, it is possible to uniformize the voids between the particles, to further restrict the powder medicine from concentrating and adhering, without decreasing the fluidity, and to surely fill the predetermined amount of powder medicine 30 from medicine storage chamber 3.

By the arrangement of medicine storage chamber 3, almost the entire powder medicine 30 provided in medicine storage chamber 3 is smoothly moved to medicine carrying chamber 8, by the force of the gravity, without remaining on its way. Accordingly, it is possible to effectively introduce powder medicine 30 into medicine carrying chamber 8.

Main body 2 includes a cylindrical projecting portion 2*a* located at a lower portion of main body 2. Projecting portion 2*a* of main body 2 is inserted into an opening 5*a* of porch-shaped pump member 5, and pump member 5 is attached to main body 2. An annular retaining claw 2*b* is formed on an outer surface of projecting portion 2*a*, and prevents pump member 5 from detaching from main body 2.

Figure 8A:
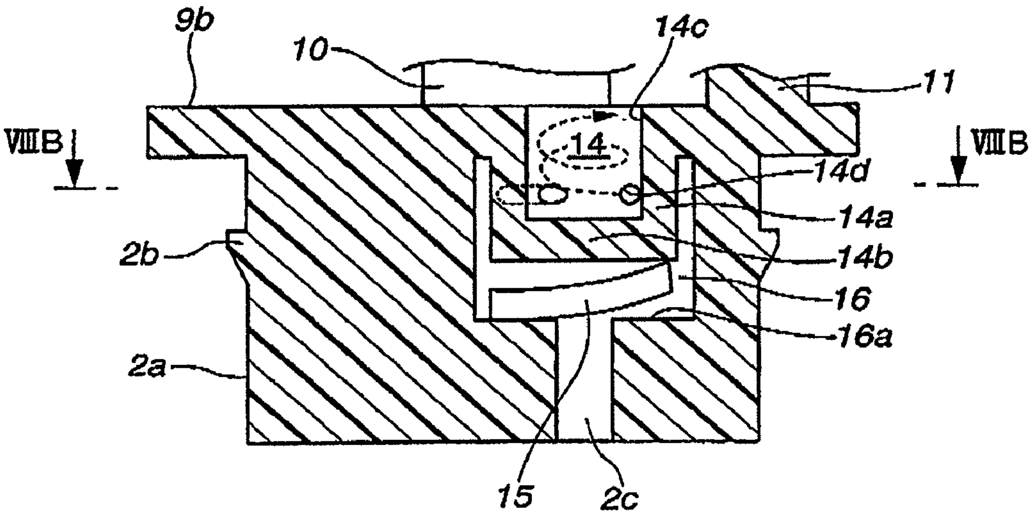
FIG. 8A is a longitudinal sectional view showing a stirred flow forming section of the powder medicine administering device of FIG. 1.
Figure 8B:
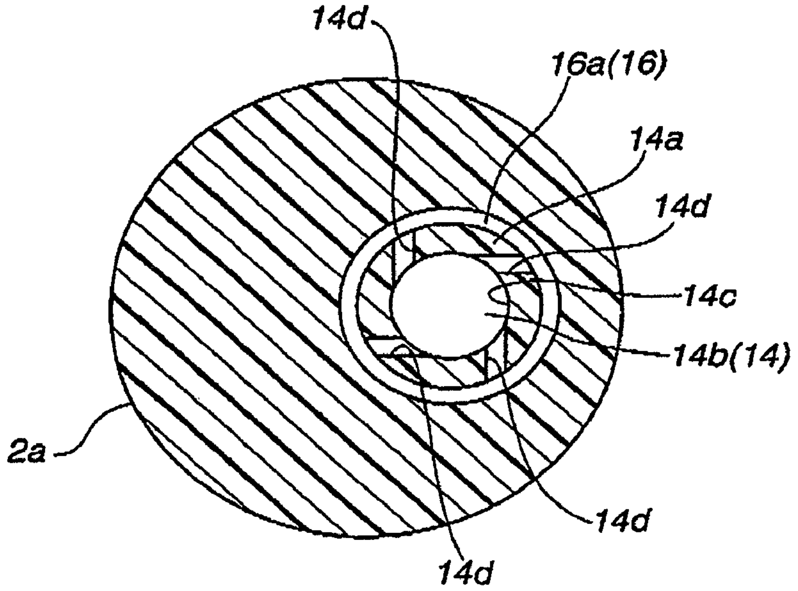
FIG. 8B is a cross sectional view taken along a section line VIIIB-VIIIB of FIG. 8A.

Projecting portion 2*a* is formed with the stirred flow forming section to promote the stirring of the air and the powder medicine. As shown in FIG. 8A, the stirred flow forming section is a stirred flow forming chamber 14 defined by a circumferential wall 14*a* and a bottom wall 14*b*. Stirred flow forming chamber 14 has a circular section. An intermediate chamber 16 is formed around (surrounds) circumferential wall 14*a* and bottom wall 14*b*. Intermediate chamber 16 is in the form of a body of revolution with a substantially U-shaped section. At a bottom surface 16*a* of intermediate chamber 16, there is provided a flexible sheet shaped check valve or non-return valve 15 arranged to open or close an air passage 2*c*. Check valve 15 allows the air to flow from air passage 2*c* into intermediate chamber 16, and prevents the air from flowing from intermediate chamber 16 into air passage 2*c*. As shown in FIG. 8B, a plurality of through holes 14*d* (four through holes 14*d* in the first embodiment) are formed in circumferential wall 14*a* of stirred flow forming chamber 14. Each through hole 14*d* extends along a circumferential direction (a tangent direction) of an inner circumferential surface 14*c* of circumferential wall 14*a*. Through holes 14*d* connect intermediate chamber 16 and stirred flow forming chamber 14. Through holes 14*d* are directed in a rotational direction (that is, in a clockwise direction or a counter-clockwise direction with respect to axial center of stirred flow forming chamber 14).

In this arrangement, when slider 7 is slid, medicine carrying chamber 8 filled with the powder medicine is closed by upper surface 9*a*, and brought to a substantially sealed state (closed state). Then, medicine carrying chamber 8 is moved over stirred flow forming chamber 14, and the powder medicine within medicine carrying chamber 8 is introduced from the upper opening into stirred flow forming chamber 14. In this state, pump member 5 is pressed by fingers, and the air within air chamber 6 is supplied under the pressure through air passage 2*c*, opened check valve 15, intermediate chamber 16, and through holes 14*d* into stirred flow forming chamber 14. In this case, each through hole 14*d* formed in inner circumferential surface 14*c* of stirred flow forming chamber 14 is directed in the same circumferential direction as described above, and accordingly the air flow introduced into stirred flow forming chamber 14 becomes the swirl flow (vortex flow) rotating along inner circumferential surface 14*c*. The swirl flow curls up the powder medicine, and the air supplied under the pressure and the powder medicine are stirred effectively. Consequently, the mixed flow of the air and the powder medicine is effectively discharged from nozzle portion 4 through medicine discharge passage 20 to the outside (the nasal cavity).

Each direction of through holes 14*d* may be inclined with reference to the up-down direction of stirred flow forming section 14 (that is, inclined upward or downward). Each of through holes 14*d* extends from a first opening opened to intermediate chamber 16, to a second opening opened to stirred flow forming chamber 14. Each of through holes 14*d* is so formed as to position the first opening above, and to position the second opening below, and it is possible to prevent the powder medicine from dropping from stirred flow forming chamber 14. Moreover, in this case, gradients of through holes 14*d* may be different from each other.

Each of through holes 14*d* is located at a position higher than a position of bottom wall 14*b*, so as to be separated from bottom wall 14*b*. Accordingly, it is possible to restrict the powder medicine introduced in stirred flow forming chamber 14 from dropping through through holes 14*d* to intermediate chamber 16. Moreover, it is possible to restrict the powder medicine from closing through holes 14, and to restrict the reduction in flow velocity of the air introduced under the pressure into stirred flow forming chamber 14.

Through holes 14*d*, air passage 2*c*, intermediate chamber 16, and stirred flow forming chamber 14 serve as part of medicine discharge passage 20. The air supplied under the pressure from air chamber 6 flows through air passage 2*c*, intermediate chamber 16, and through holes 14*d*.

In the device according to the first embodiment of the present invention, (the circumferential surface of) inner cylindrical portions 2*j* and 2*k* of the lower part of medicine storage chamber 3 are arranged to be inclined radially inward toward opening 2*q* of the bottom portion. Accordingly, it is possible to gather powder medicine 30 to medicine carrying chamber 8 connected with opening 2*q*, and to introduce the predetermined amount of powder medicine 30 to medicine discharge passage 20 by moving medicine carrying chamber 8. Accordingly, it is possible to restrict powder medicine 30 from remaining in medicine storage chamber 3.

In this case, main body 2 is formed with medicine storage chamber 3, and slider 7 is formed with medicine carrying chamber 8 having a volume smaller than a volume of medicine storage chamber 3. Accordingly, it is possible to further reduce the size of slider 7 serving as the movable member, and to relatively simplify the arrangement of main body 2 for movably supporting slider 7.

In the device according to the first embodiment of the present invention, the gradient of (the circumferential surface of) inner cylindrical portion 2*k* is larger than the gradient of (the circumferential surface of) inner cylindrical portion 2*j* located above inner cylindrical portion 2*k*. Accordingly, it is possible to vary the movement of powder medicine 30 within medicine storage chamber 3 by the variation between the gradients of inner cylindrical portions 2*k* and 2*j*. It is possible to uniformize the voids between the particles, without detracting from the fluidity. Accordingly, it is possible to restrict powder medicine 30 from collecting and adhering within medicine storage chamber 3.

In the device according to the first embodiment of the present invention, the lower portion (bottom portion) of medicine storage chamber 3 is eccentric to the center C of the upper portion of medicine storage chamber 3. Accordingly, it is possible to vary the movement of powder medicine 30 in accordance with the position of powder medicine 30 within medicine storage chamber 3. Therefore, it is possible to uniformize the voids between the particles, without detracting from the fluidity of powder medicine 30. Moreover, it is possible to restrict powder medicine 30 from aggregating and solidifying within medicine storage chamber 3.

In the device according to the first embodiment of the present invention, stirred flow forming chamber 14 serving as the medicine receiving chamber is formed under medicine carrying chamber 8 when medicine carrying chamber 8 is connected with medicine discharge passage 20. Accordingly, it is possible to restrict the reverse flow of the powder medicine to the upstream side of stirred flow forming chamber 14, and to restrict the powder medicine from remaining in powder medicine administering device 1.

In the device according to the first embodiment of the present invention, stirred flow forming chamber 14 is arranged to stir powder medicine 30 provided in medicine discharge passage 20, and the air supplied under the pressure from the pump member 5. Accordingly, it is possible to restrict the powder medicine from remaining within powder medicine administering device 1, and to discharge the powder medicine in the more diffuse state.

In the device according to the first embodiment of the present invention, there are provided through holes 14*d* serving as the air passage for introducing the air flow in the tangent direction of inner circumferential surface 14*c* of stirred flow forming chamber 14. Accordingly, it is possible to produce the stirred flow within stirred flow forming chamber 14, to sufficiently stir the powder medicine and the air supplied under the pressure, by the stirred flow, and to restrict the powder medicine from remaining in powder medicine administering device 1.

In the device according to the first embodiment of the present invention, slider 7 is further projected outwards with reference to the outer surface of main body 2 when medicine carrying chamber 8 is connected with medicine discharge passage 20 than when medicine carrying chamber 8 is connected with opening 2*q* of medicine storage chamber 3. Accordingly, it is possible to prompt the user to operate to decrease the amount of projection of slider 7, and to put medicine carrying chamber 8 back to the position where medicine carrying chamber 8 is connected with opening 2*q*, at the nonuse (after the use).

Figure 9:
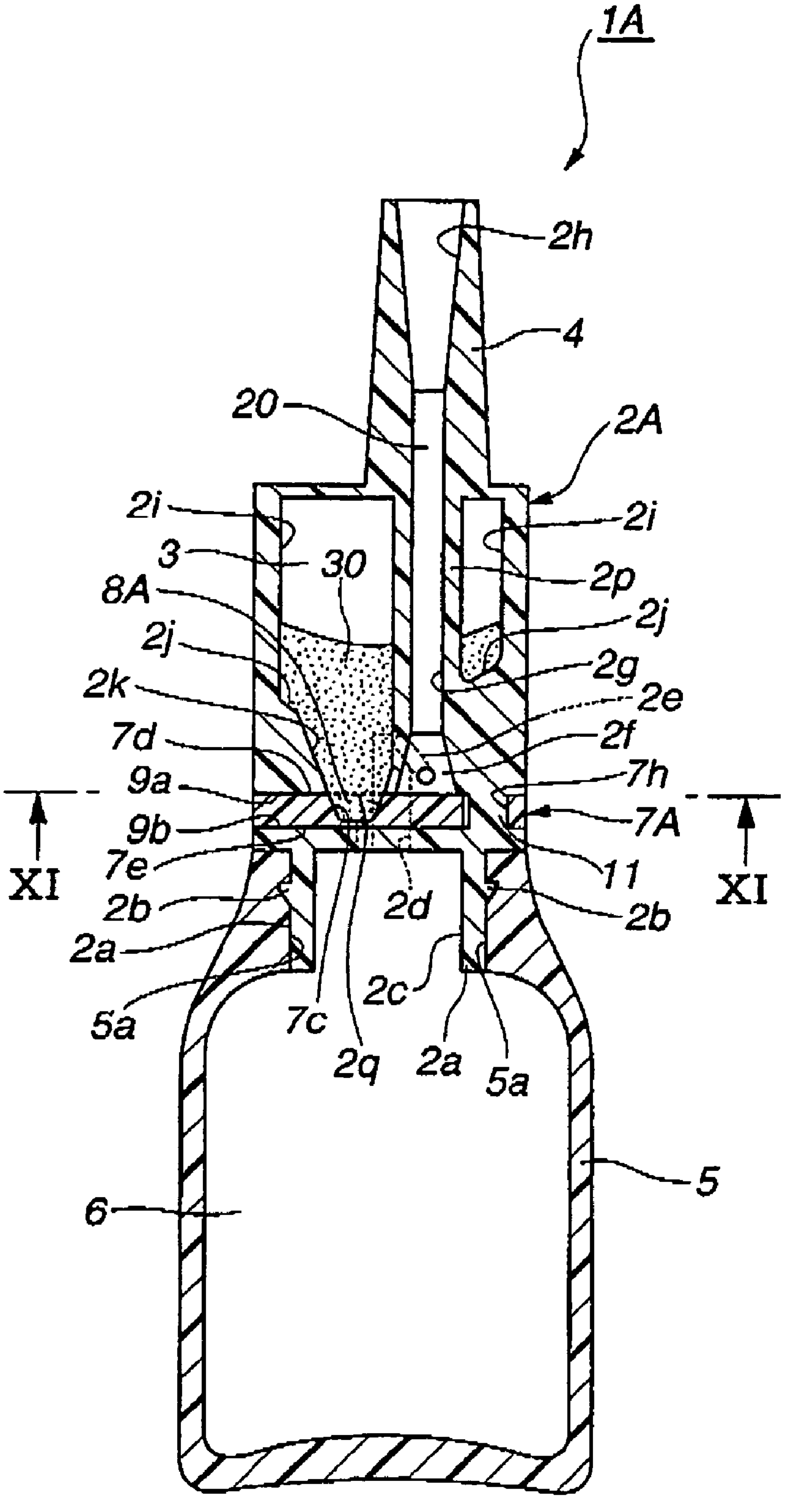
FIG. 9 is a longitudinal sectional view showing a powder medicine administering device being in the administration disable state, and according to a second embodiment of the present invention.
Figure 10:
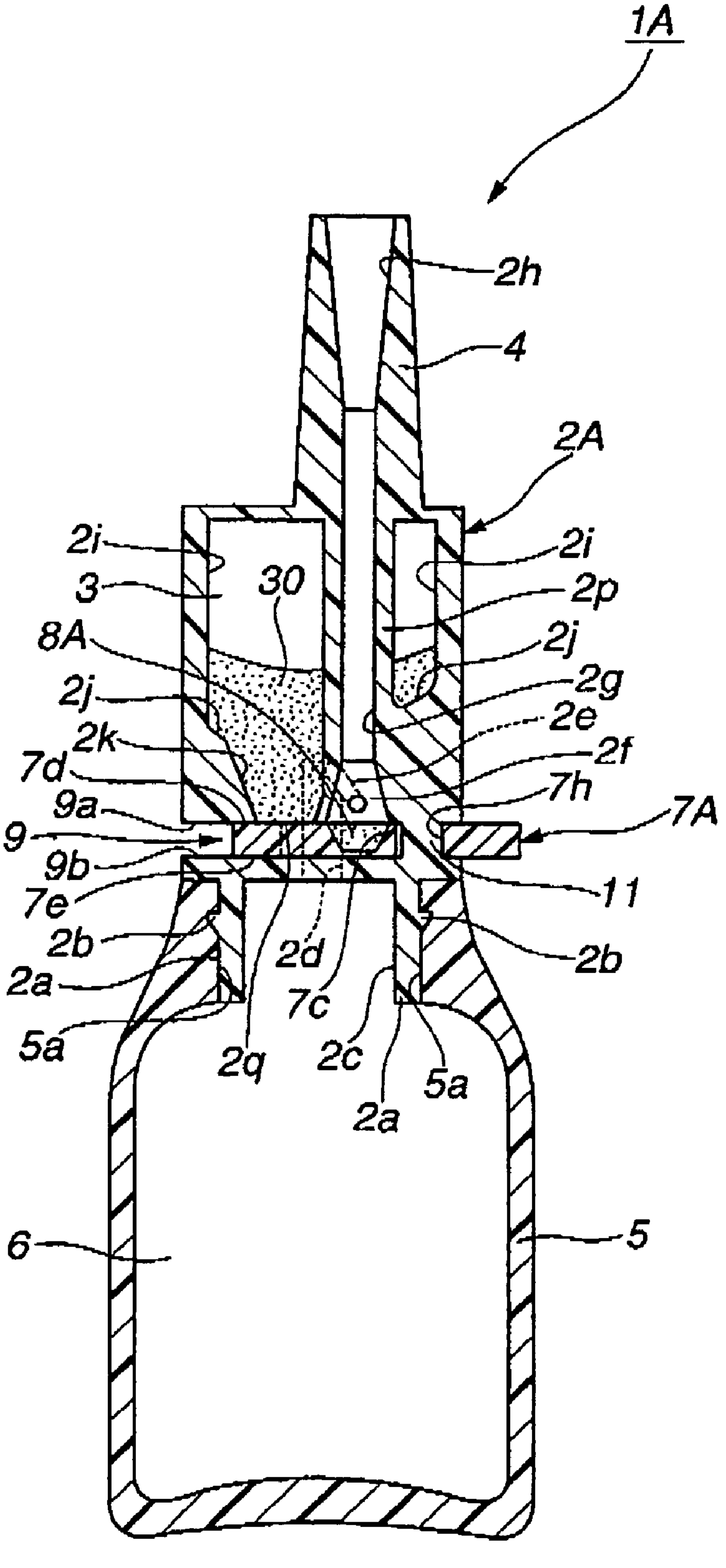
FIG. 10 is a longitudinal sectional view showing a powder medicine administering device of FIG. 9, being in the administration enable state.
Figure 11:
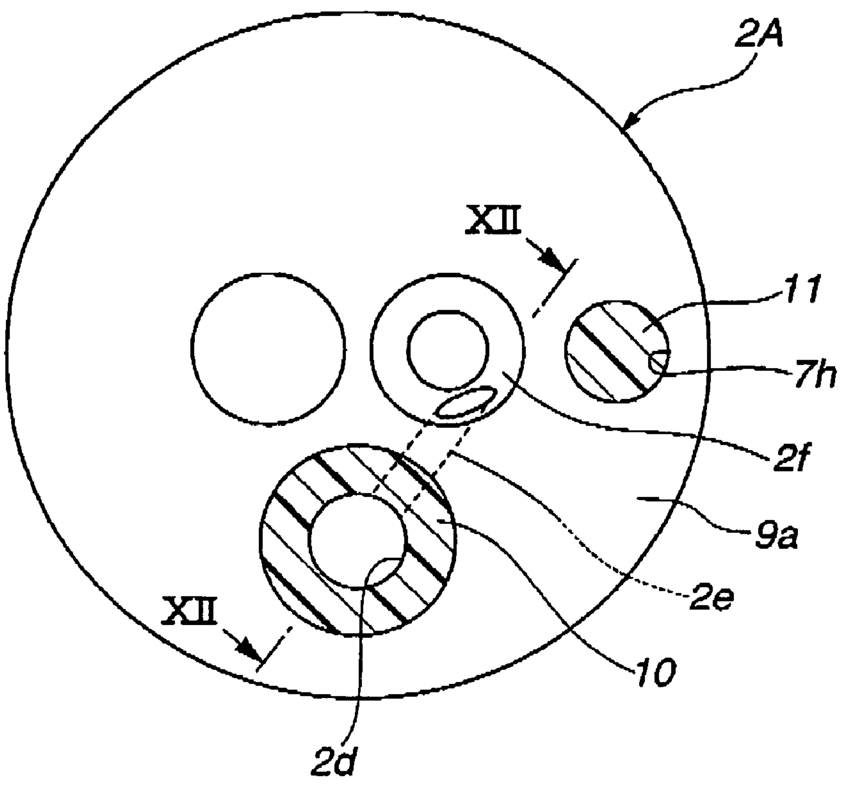
FIG. 11 is a cross sectional view taken along a section line XI-XI of FIG. 9.
Figure 12:
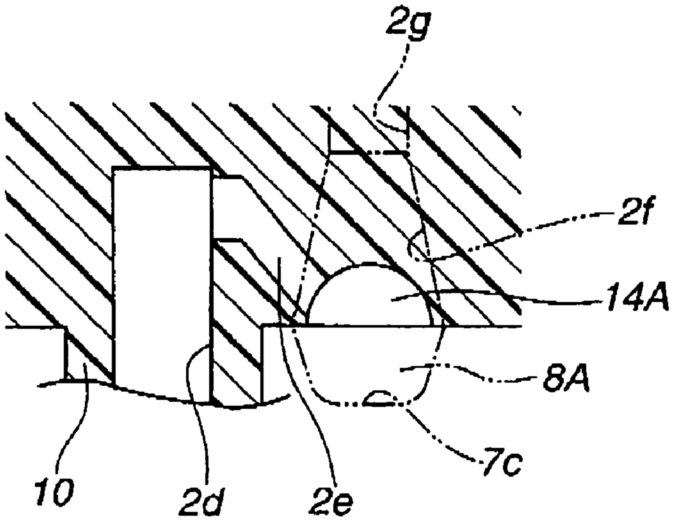
FIG. 12 is a longitudinal sectional view taken along a section line XII-XII of FIG. 11, and showing a stirred flow forming section formed in the powder medicine administering device.

FIG. 9 shows a longitudinal sectional view showing a powder medicine administering device being in the administration disable state, and according to a second embodiment of the present invention. FIG. 10 shows a longitudinal sectional view of FIG. 9, being in the administration enable state. FIG. 11 shows a cross sectional view taken along a section line XI-XI of FIG. 9, and showing the powder medicine administering device being in the medicine enable state. FIG. 12 shows a longitudinal sectional view taken along a section line XII-XII of FIG. 11. The powder medicine administering device of FIG. 9 is substantially identical to the structure of FIG. 3 in most aspects as shown by the use of the same reference numerals.

In the device according to the first embodiment of the present invention, main body 2 is formed with the stirred flow forming section separately from medicine carrying chamber 8 and so on. In the device according to the second embodiment of the present invention, medicine carrying chamber 8A is arranged to serve as the stirred flow forming section with medicine discharge passage 20 when medicine carrying chamber 8A is moved at a position where medicine carrying chamber 8A is connected with medicine discharge passage 20.

That is, in the device according to the second embodiment of the present invention, main body 2A is formed with air passage 2*c* having a diameter larger than a diameter of the air passage of the powder medicine administering device according to the first embodiment. Air passage 2*c* is opened (connected) to air chamber 6. Main body 2 is formed with an air passage 2*d* opened in an upper surface of air passage 2*c*, and arranged to pass through cylindrical bridge portion 10 connecting (extending between) upper surface 9*a* and lower surface 9*b* of gap 9. Main body 2 is formed with an air passage 2*e* extending obliquely downward. A lower end (downstream end) of air passage 2*e* is opened in the inner circumferential surface of inner cylindrical portion 2*f* formed in a lower portion of cylindrical portion 2*p*. Air passages 2*c*, 2*d* and 2*e* serve as part of medicine discharge passage 20 connecting air chamber 6 and inner cylindrical portion 2*h* of the end portion of nozzle portion 4. The air supplied under the pressure from air chamber 6 passes through air passages 2*c*, 2*d* and 2*e*.

Moreover, in the administration enable state in which slider 7A is slid (as shown in FIG. 10), A-shaped inner cylindrical portion 2*f* is connected with V-shaped recessed portion 7*c* (medicine carrying chamber 8A) formed in slider 7A. Inner cylindrical portion 2*f* has a diameter larger at a upper position than a diameter at a lower position.

Moreover, in the device according to the second embodiment of the present invention, air passage 2*e* upstream of medicine carrying chamber 8 crosses air passages 2*f* and 2*g* downstream of medicine carrying chamber 8. Accordingly, it is possible to promote the disturbance of the air near medicine carrying chamber 8A when medicine carrying chamber 8A is connected with medicine discharge passage 20, and to promote the agitation of the air and powder medicine 30 within medicine carrying chamber 8A.

In the device according to the second embodiment of the present invention, air passage 2*e* is directed to the bottom portion of medicine carrying chamber 8 to extend obliquely downward, and the air supplied under the pressure from air chamber 6 is sprayed to powder medicine 30 within medicine carrying chamber 8. Then, powder medicine 30 and the air are stirred, and curled up. Consequently, the stirred flow is formed to rise and rotate the air and the powder medicine, and discharged from inner cylindrical portion 2*h* of the end portion of nozzle member 4. Accordingly, it is possible to readily lead the powder medicine to the mucous membrane, and to readily take in the powder medicine from the mucous membrane into the body.

As shown in FIGS. 8 and 9, medicine carrying chamber 8A is opened in upper surface 7*d* of slider 7A. Medicine carrying chamber 8A is formed as bottom recessed portion 7*c* connected with inner cylindrical portion 2*k*. In this case, recessed portion 7*c* has the smooth bottomed surface (for example, the curved shape). Accordingly, it is possible to smoothly flow the air flow sprayed to recessed portion 7*c*, and to restrict the air flow from weakening. Moreover, it is possible to promote to stir the powder medicine within recessed portion 7*c* (medicine carrying chamber 8) and the air supplied under the pressure, and to restrict the powder medicine from remaining in recessed portion 7*c*.

In the device according to the second embodiment of the present invention, it is also possible to attain the same effect as the first embodiment of the present invention. Moreover, powder medicine carrying chamber 8A serves as part of the stirred flow forming section when powder medicine carrying chamber 8A is connected with medicine passage 20, and it is possible to further simplify the structure, relative to the structure having medicine carrying chamber 8A and the stirred flow forming section separately.

In the device according to the second embodiment of the present invention, air passage 2*d*, air passage 2*e*, and inner cylindrical portions 2*f*, 2*g* and 2*h* are formed in the bent state. Accordingly, it is possible to promote burble and turbulence of the air flow, and to stir the powder medicine and the air sufficiently.

In the device according to the second embodiment of the present invention, medicine carrying chamber 8A is bottom recessed portion 7*c* opened in upper surface 7*b* of slider 7A. The powder medicine does not come into an interspace between lower surface 7*e* of slider 7A and lower surface 9*b* of gap 9.

In the device according to the second embodiment of the present invention, medicine discharge passage 20 from air chamber 6 to inner cylindrical portion 2*h* of the end portion of nozzle portion 4 is constantly held in the connected state (connection state), irrespective of the positions of slider 7A. There is no need to consider the increasing of the pressure in air chamber 6 by pressing pump member 5 in the closed state of air chamber 6. Accordingly, it is possible to decrease the rigidity and the strength of main body 2A, pump member 5 and so on, and to promote the size reduction of powder medicine administering device 1.

Figure 13:
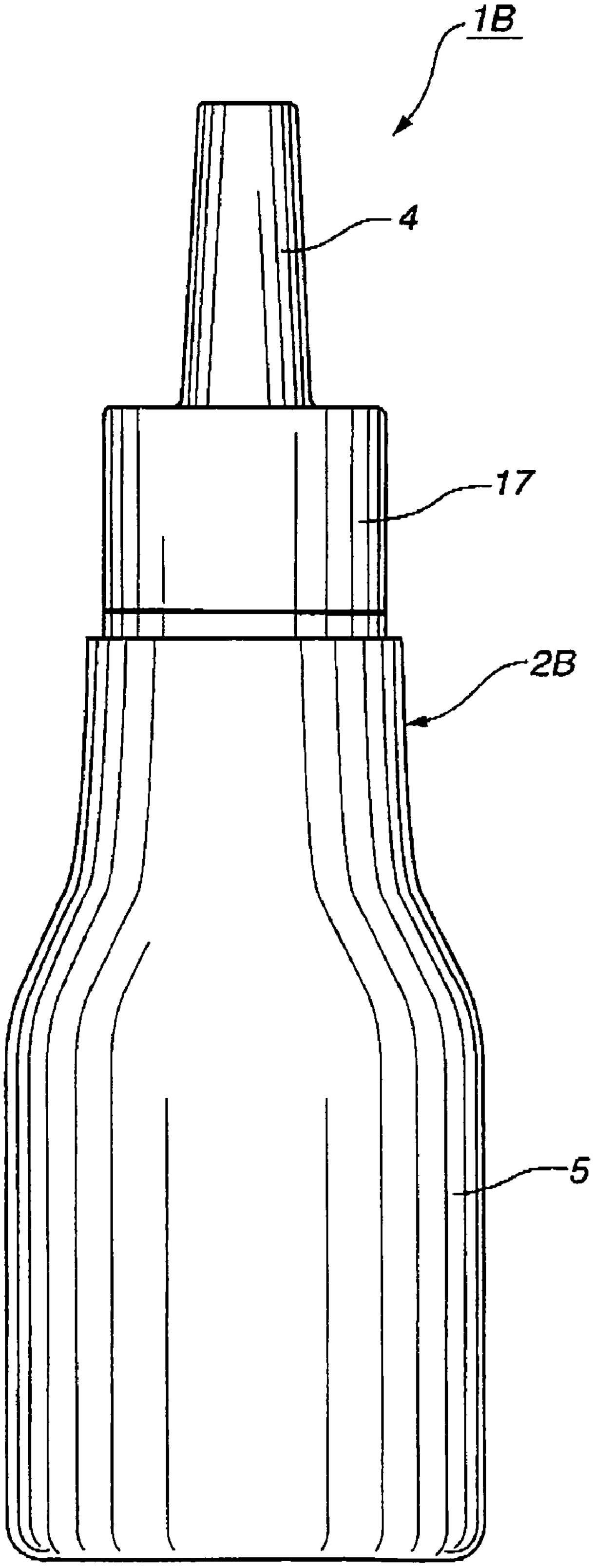
FIG. 13 is a side view showing a powder medicine administering device being in the administration disable state, and according to a third embodiment of the present invention.
Figure 14:
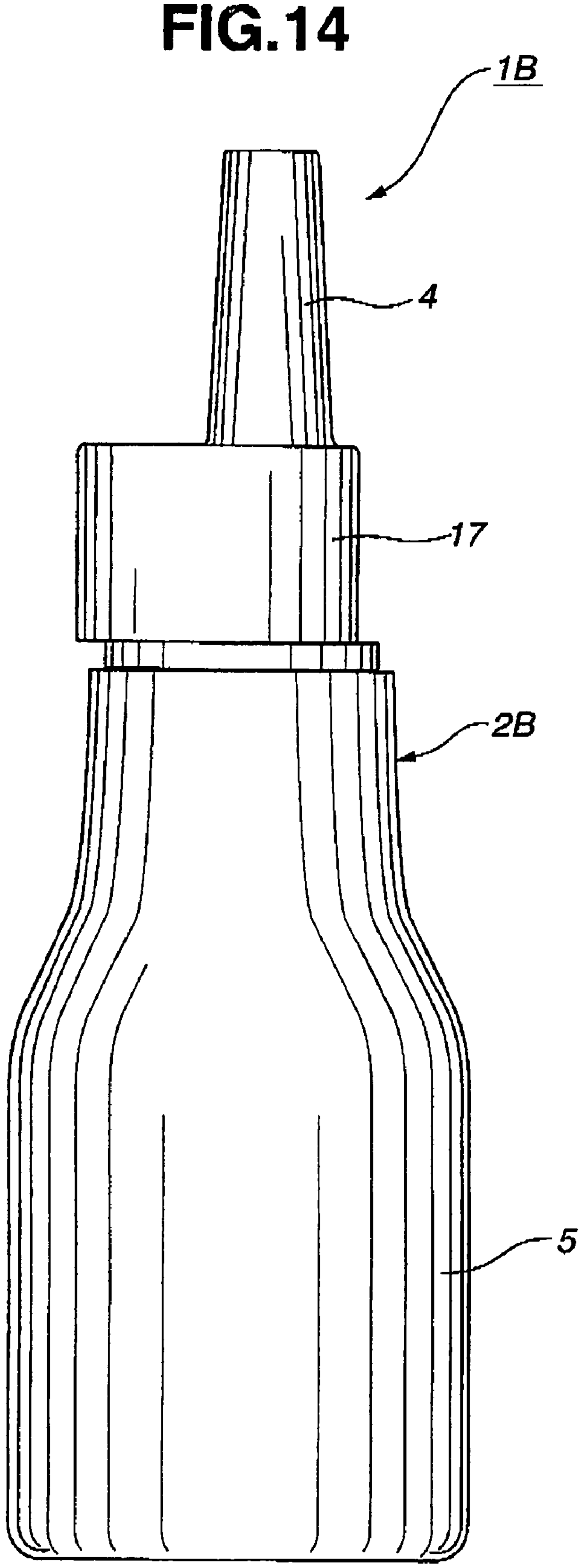
FIG. 14 is a side view showing the powder medicine administering device of FIG. 13, being the administration enable state.
Figure 15:
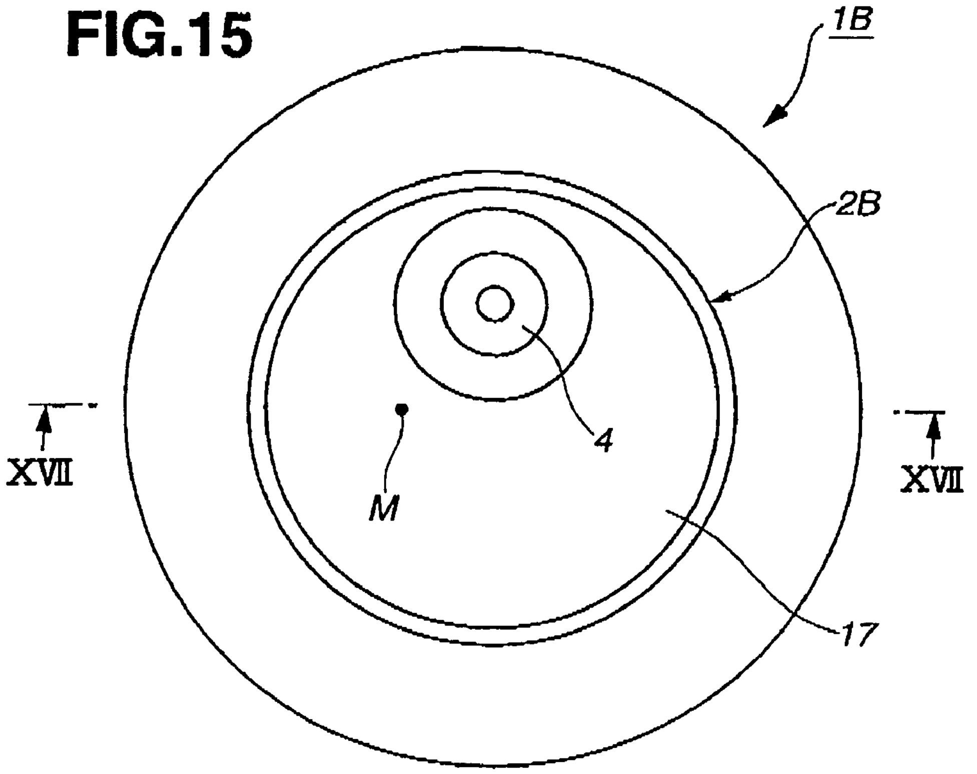
FIG. 15 is a plan view showing the powder medicine administering device of FIG. 13, being in the administration disable state.
Figure 16:
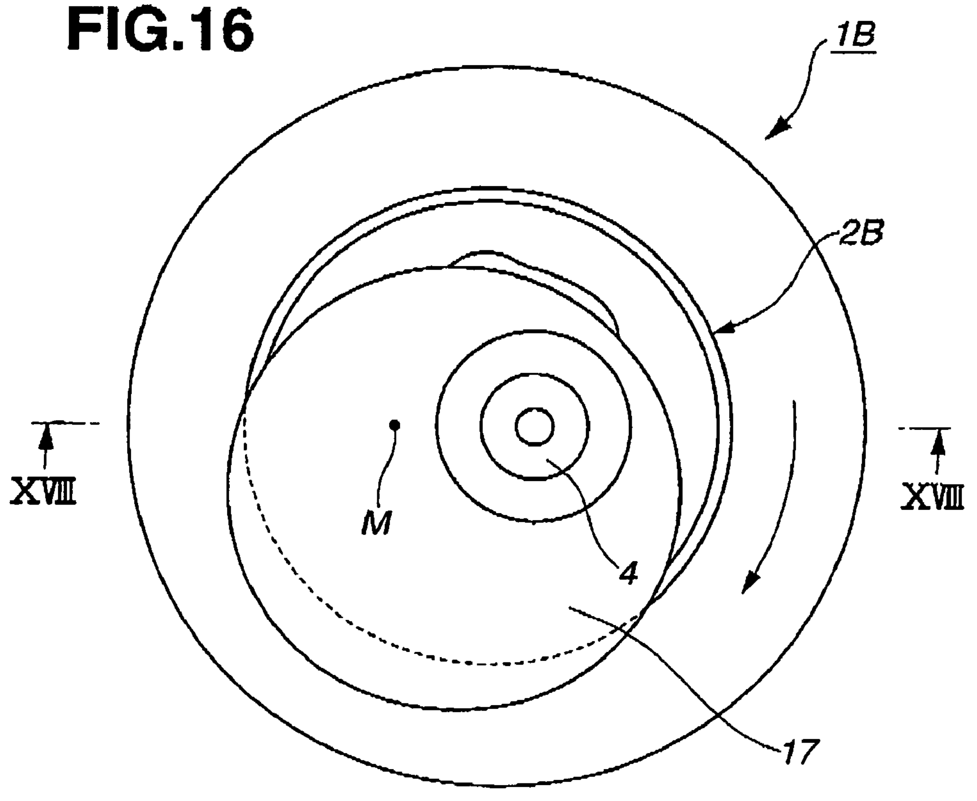
FIG. 16 is a plan view showing the powder medicine administering device of FIG. 14, being in the administration enable state.
Figure 17:
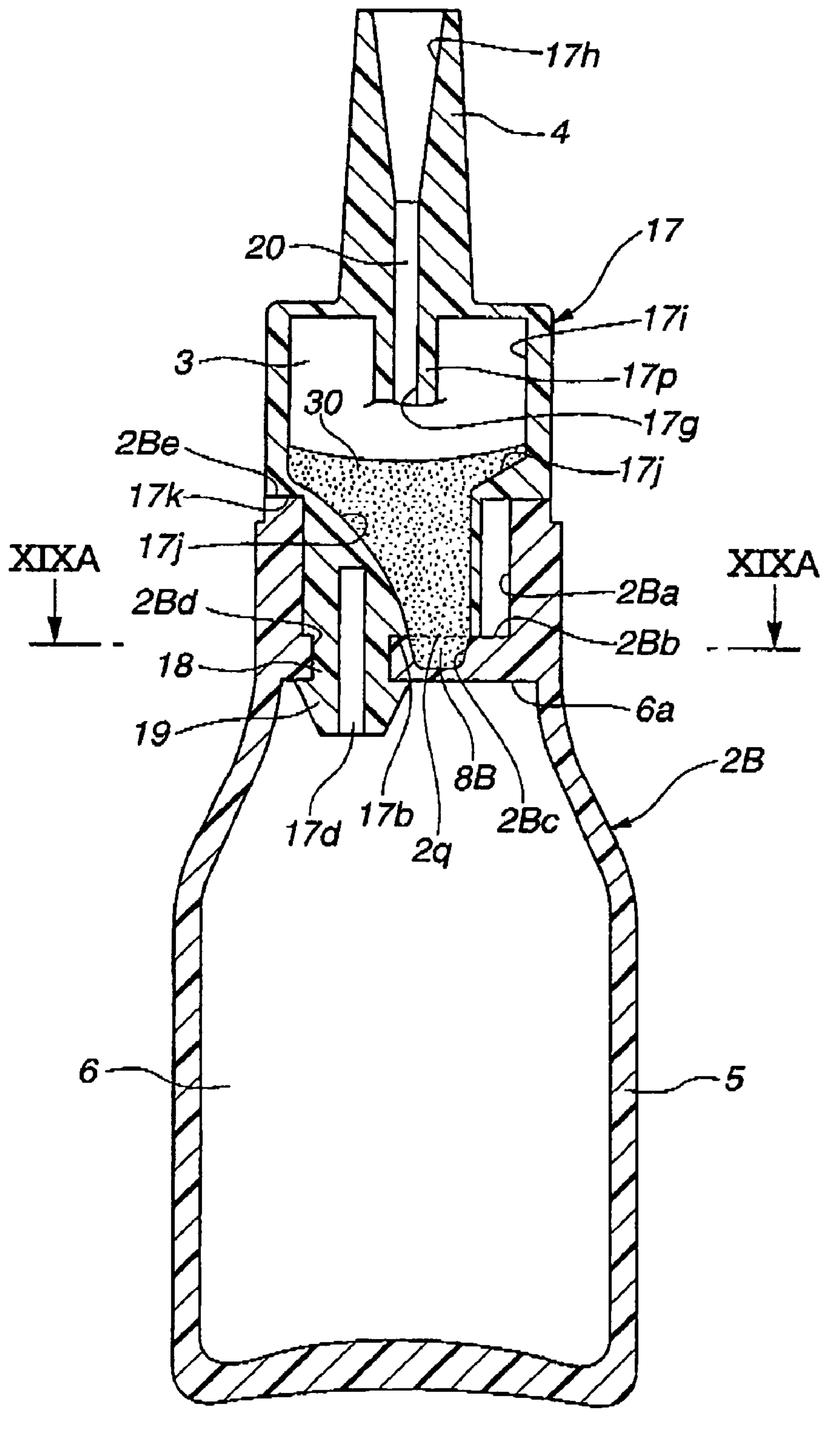
FIG. 17 is a longitudinal sectional view taken along a section line XVII-XVII of FIGS. 15 and 19A, and showing the powder medicine administrating device being in the administration disable state.
Figure 18:
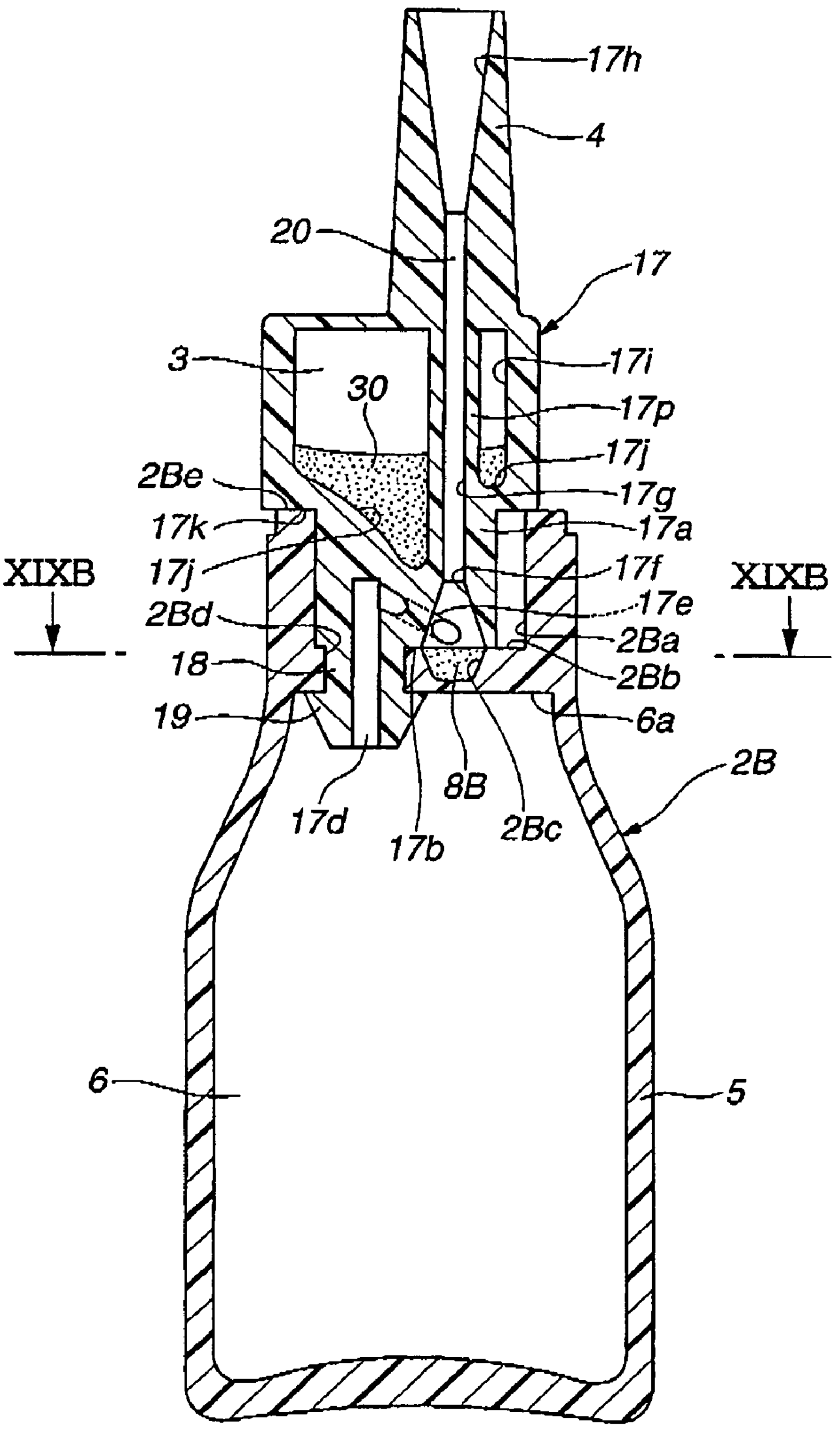
FIG. 18 is a longitudinal sectional view taken along a section line XVIII-XVIII of FIGS. 16 and 19B, and showing the powder medicine administrating device being in the administration enable state.
Figure 19A:
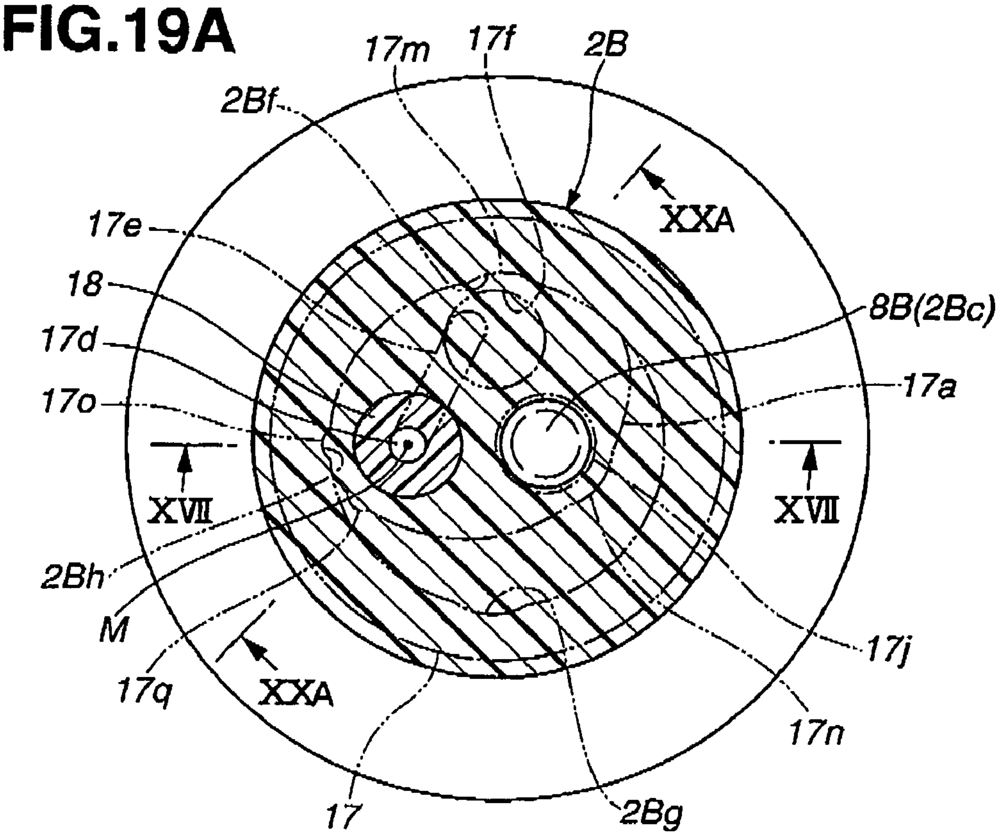
FIG. 19A is a cross sectional view taken along a section line XIXA-XIXA of FIG. 17.
Figure 19B:
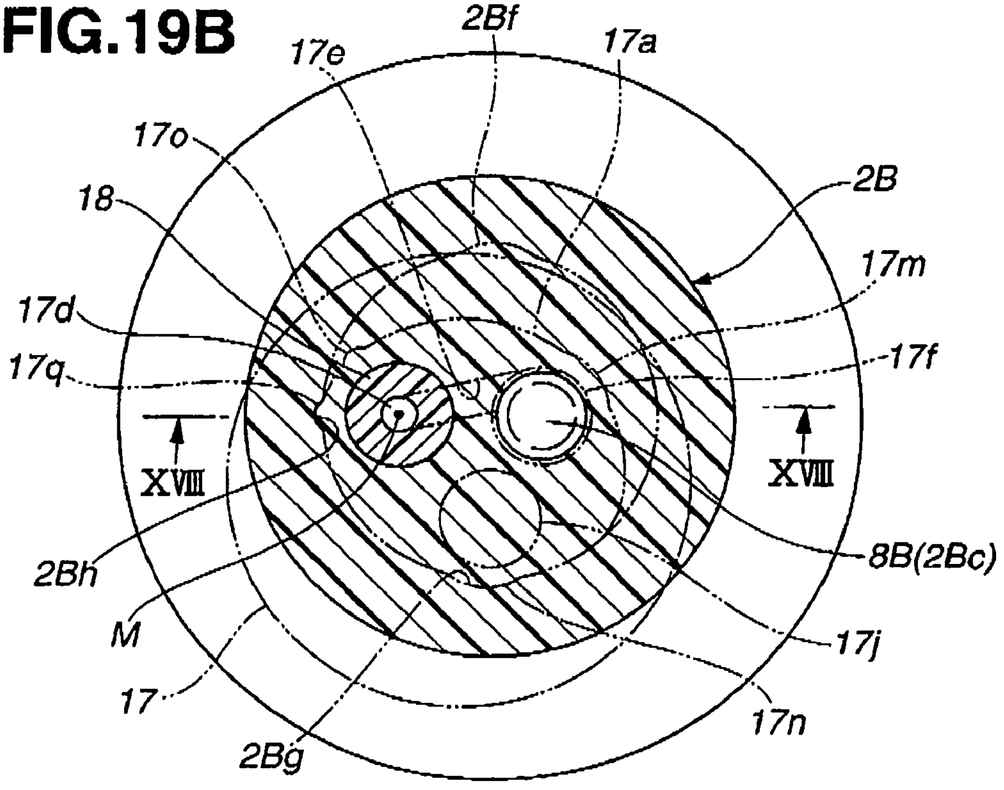
FIG. 19B is a cross sectional view taken along a section line XIXB-XIXB of FIG. 18.
Figure 20A:
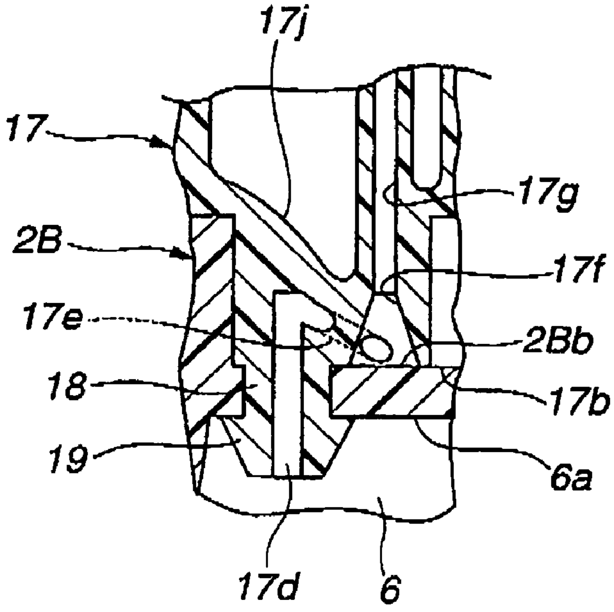
FIG. 20A is a longitudinal sectional view taken along a section line XXA-XXA of FIG. 19A.
Figure 20B:
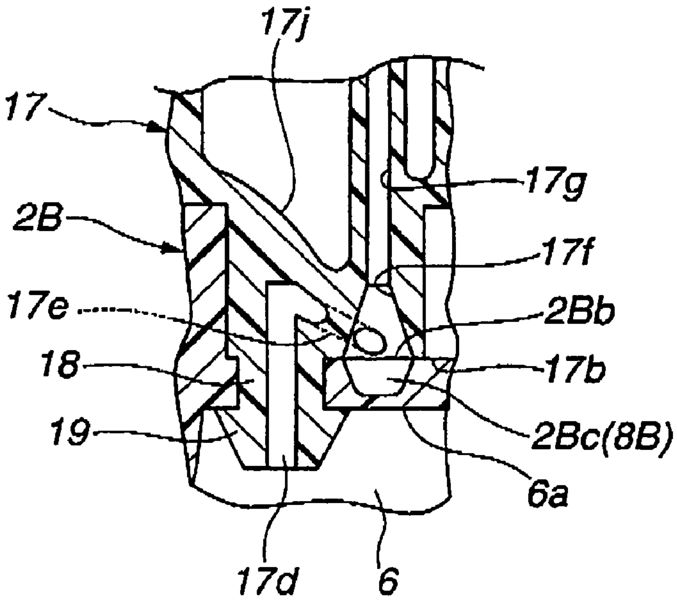
FIG. 20B is a longitudinal sectional view taken along a section line XVIII-XVIII of FIG. 19B.

(Third embodiment) FIG. 13 shows a side view showing a powder medicine administering device being in the administering disable state, and according to a third embodiment of the present invention. FIG. 14 shows a side view showing the powder medicine administering device of FIG. 13, and being in the administering enable state. FIG. 15 shows a plan view showing the powder medicine administering device of FIG. 13, being in the administration disable state. FIG. 16 shows a plan view showing the powder medicine administering device of FIG. 14, being in the administration enable state. FIG. 17 shows a longitudinal sectional view taken along a section line XVII-XVII of FIGS. 15 and 19A, and showing the powder medicine administering device being in the administration disable state. FIG. 18 shows a longitudinal sectional view taken along a section line XVIII-XVIII of FIGS. 16 and 19B, and showing the powder medicine administrating device being in the administration enable state. FIG. 19A shows a cross sectional view taken along a section line XIXA-XIXA of FIG. 17. FIG. 19B shows a cross sectional view taken along a section line XIXB-XIXB of FIG. 18. FIG. 20A shows a longitudinal sectional view taken along a section line XXA-XXA of FIG. 19A. FIG. 20B shows a longitudinal sectional view taken along a section line XVIII-XVIII of FIG. 19B. The powder medicine administering device of FIG. 13 is substantially identical to the structure of FIG. 1 in most aspects as shown by the use of the same reference numerals.

In the devices according to the first and second embodiments of the present invention, medicine storage chambers 3 are formed in main bodies 2 and 2A respectively, and medicine carrying chamber 8 and 8A are formed in the respective sliders 7 and 7A serving as the movable members. In the device according to the third embodiment of the present invention, a medicine carrying chamber 8B is formed in a main body 2B, and medicine storage chamber 3 is formed in a movable member (movable body) 17. Medicine storage chamber 3 is movable with respect to medicine carrying chamber 8B, unlike the devices according to the first and second embodiments.

That is, movable member 17 is slidably connected with an upper portion of main body 2B including pump portion 5 to be rotatably (swingably) slid (moved) in a direction perpendicular to the axial direction (the up-down direction) of powder medicine administering device 1B. Movable member 17 includes nozzle portion 4, and forms a substantially upper half part of powder medicine administering device 1B. Powder medicine administering device 1B has relatively simple two-part structure separated into upper and lower members. Accordingly, it is possible to gain a simple structure of powder medicine administering device 1B, relative to devices according to the first and second embodiments of the present invention. Moreover, it is possible to restrict powder medicine 30 from remaining within medicine storage chamber 3 because the frequency of movement of medicine storage chamber 3 is increased.

As shown in FIGS. 17 and 18, a cylindrical recessed portion 2Ba is formed in an upper surface 2Be of main body 2B. A bottom recessed portion 2Bc and a through hole 2Bd are formed in a bottom surface 2Bb of cylindrical recessed portion 2Ba. Bottom recessed portion 2Bc is in the form of V-shape. Through hole 2Bd is connected with air chamber 6.

On the other hand, movable member 17 has a stepped shape, and includes a small diameter portion 17*a* projecting downwards. In a state in which small diameter portion 17*a* is inserted into recessed portion 2Ba of main body 2B, small diameter portion 17*a* of movable member 17 is arranged to be slid (rotated) within recessed portion 2Ba. In this state, bottom surface 17*b* of small diameter portion 17*a* is slidably abutted on bottom surface 2Bb of recessed portion 2Ba. Contrarily, a small interspace (clearance) is disposed between upper surface 2Be of main body 2B and a stepped surface 17*k* of small diameter portion 17*a*. That is, in the device according to the third embodiment of the present invention, bottom surface 2Bb serves as a sliding surface slidably abutting on movable member 17.

Moreover, bottom surface 17*b* of small diameter portion 17*a* is formed with a substantially cylindrical projecting portion 18 projecting downward. Projecting portion 18 is inserted through through hole 2Bd formed in bottom surface 2Bb of recessed portion 2Bc. A raised portion 19 is formed at a penetrating end portion of projecting portion 18, and retained by upper surface 6*a* of air chamber 6. Consequently, movable member 17 is supported by main body 2B.

Movable member 17 is supported on through hole 2Bd serving as a bearing. Movable member 17 is arranged to rotate (slide) about a center M (as shown in FIGS. 15, 16, 19A, and 19B) of projecting portion 18 (through hole 2Bd) so that powder medicine administering device 1B is changed over between the administration disable state as shown in FIGS. 13, 15, 17, 19A, and 20A and the administration enable state as shown in FIGS. 14, 16, 18, 19B, and 20B. In this case, movable member 17 is received in the administration disable state, and projected from the outer surface of powder medicine administrating device 1B (the circumferential surface of main body 2B) in the administration enable state. Accordingly, the user can judge whether powder medicine administering device 1B is in the administration enable state or in the administration disable state, by the change in the outer appearance. It is possible to prompt the user to return to the administration disable state by operation to restore the outwards projecting portion of slider 7 after the use.

In the device according to the third embodiment of the present invention, raised portions 17*m*, 17*n*, 17*o*, and 17*q* are formed on an outer circumferential surface of small diameter portion 17*a*. Recessed portions 2Bf, 2Bg and 2Bh are formed in an inner circumferential surface of recessed portion 2Ba. In the administration disable state as shown in FIG. 19A, raised portion 17*m* is engaged with recessed portion 2Bf, and raised portion 17*o* is engaged with recessed portion 2Bh. In the administration enable state as shown in FIG. 19B, raised portion 17*n* is engaged with recessed portion 2Bg, and raised portion 17*q* is engaged with recessed portion 2Bh. By this arrangement, it is possible to improve the accuracy of the positioning and the retention (holding) of the position, and to improve the operational feeling by the engagement (fitting) between the recessed portion and the raised portion.

As shown in FIGS. 17~20B, medicine storage chamber 3 and medicine discharge passage 20 are formed in movable member 17, to have the structure substantially identical to the device according to the second embodiment of the present invention. That is, inner cylindrical portion 17*i* with the substantially uniform circular section is smoothly connected with inner cylindrical portion 17*j* inclined radially inward toward opening 2*q*. Medicine storage chamber 3 is in the form of the shape substantially identical to medicine storage chambers 3 of powder medicine administering devices 1 and 1A according to the first and second embodiments. Medicine storage chamber 3 includes cylindrical portion 17*p* extending in the up-down direction within medicine storage chamber 3. The portion within cylindrical portion 17 serves as medicine discharge passage 20 (17*f*, 17*g* and 17*h*).

In the device according to the third embodiment of the present invention, medicine carrying chamber 8B and medicine discharge passage 20 near medicine carrying chamber 8B serve as the stirred flow forming section. That is, an air passage 17*d* and an air passage 17*e* are formed in movable member 17, and air passage 17*d* extends in the axial direction of powder medicine administering device 1B, at a substantially central portion of projecting portion 18. Air passage 17*d* is opened to air chamber 6. Air passage 17*e* extends obliquely downward by bending the upper portion of air passage 17*d*. A lower portion (downstream end portion) of air passage 17*e* is opened in the inner circumferential surface of inner cylindrical portion 17*f*.

In the administration disable state as shown in FIGS. 17 and 19A, inner cylindrical portion 17*j* of movable member 17 is connected with recessed portion 2Bc formed in main body 2B, and medicine carrying chamber 8B serves as the bottom portion of medicine storage chamber 3. In the administration enable state as shown in FIGS. 18 and 19B, inner cylindrical portion 17*f* of movable member 17 is connected with recessed portion 2Bc of main body 2B, and medicine carrying chamber 8B serves as part of medicine discharge passage 20.

Accordingly, in the administration enable state, the air supplied under the pressure from air chamber 6 is sprayed to powder medicine 30 within medicine carrying chamber 8B, and stirs and curls up powder medicine 30. Consequently, there is formed the stirred flow of the powder medicine and the air which rise and rotate, and the stirred flow is discharged from inner cylindrical portion 17*h* of end portion of nozzle portion 4 to the outside (the nasal cavity).

As shown in FIG. 20A, in the device according to the third embodiment of the present invention, it is also possible to always hold a connecting state (connection state) in which medicine discharge passage 20 from air chamber 6 to inner cylindrical chamber 17*h* of the end portion of nozzle portion 4 is connected, in both the administration enable state and administration disable state, irrespective of position of movable member 17 (relative position of medicine carrying chamber 8B with respect to main body 2B). Accordingly, there is not need to consider the increase in the pressure within air chamber 6 by pressing pump member 5 in the airtight (closed) state of air chamber 6. Therefore, it is possible to omit air introduction portion 12, and to lower the rigidity and the strength of movable member 17, pump member 5, and so on. Moreover, it is possible to contribute the size reduction and the reduction in the manufacturing cost of powder medicine administering device 1B.

In the device according to the third embodiment of the present invention, it is possible to attain the same effect as the devices according to the first and second embodiments of the present invention. Moreover, movable member 17 formed with medicine storage chamber 3 is slid with reference to main body 2B, and it is possible to reduce the number of the components moving relatively, and sliding parts of the components. Accordingly, it is possible to simplify the arrangement in which the medicine carrying chamber is slid (moved) relatively. Moreover, it is possible to restrict powder medicine 30 from remaining within medicine storage chamber 3 because the frequency of movement of medicine storage chamber 3 is increased.

The embodiments of the present invention discloses the powder medicine administering devices for the nasal cavity. However, the present invention is applicable to powder medicine administering devices arranged to discharge the powder medicine, except for the nasal cavity.

In the devices according to the embodiments of the present invention, the slider and the movable member are rotationally moved (slid). However, the slider and the movable member may be linearly moved (slid).

In the devices according to the embodiments of the present invention, the movable member is projected from the outer surface of the main body in the administration enable state, and received inside the main body in the administration disable state. Conversely, it is optional to project the movable member from the outer surface of the main body in the administration disable state, and to receive the movable member inside the main body in the administration enable state.

In the devices according to the embodiments of the present invention, the main body is formed with the medicine storage chamber, and the movable member is formed with the medicine carrying chamber.

By this arrangement, it is possible to further reduce the size of the movable member, and to simplify the support structure of the main body for movably supporting the movable member.

In the devices according to the embodiments of the present invention, the movable member is formed with the medicine storage chamber, and the main body is formed with the medicine carrying chamber.

By this arrangement, the frequency of the movement of the medicine storage chamber is increased, and the frequency of variation of the acceleration of the powder medicine is increased. Consequently, it is possible to restrict the powder medicine from remaining in the medicine storage chamber.

In the devices according to the embodiments of the present invention, there is provided the stirred flow forming chamber to stir the air supplied under the pressure by the air supply mechanism or section, and the powder medicine introduced into the medicine discharge passage.

By this arrangement, it is possible to discharge the powder medicine in the more diffuse state, and to surely administer the powder medicine into the bottom of the nasal cavity. Moreover, it is possible to restrict the powder medicine from remaining within the powder medicine administering device.

In the devices according to the embodiments of the present invention, the medicine carrying chamber serves as at least part of the stirred flow forming chamber when the medicine carrying chamber is connected with the medicine discharge passage.

By this arrangement, it is possible to simplify the arrangement of the powder medicine administering device, relative to the arrangement which is separately provided with the stirred flow forming chamber.

In the devices according to the embodiments of the present invention, the medicine carrying chamber serves as at least part of the medicine discharge passage when the medicine carrying chamber is connected with the medicine discharge passage, and the medicine receiving chamber is located below the medicine carrying chamber.

By this arrangement, it is possible to more surely discharge the powder medicine in the medicine carrying chamber, and to restrict the reverse flow of the powder medicine from the medicine receiving chamber to the upstream side of the medicine discharge passage. Accordingly, it is possible to restrict the powder medicine from remaining in the powder medicine administering device.

In the device according to the embodiments of the present invention, the side wall surface of the medicine receiving chamber is the circumferential wall surface. The medicine discharge passage upstream of the medicine receiving chamber is formed along the tangent direction of the circumferential wall surface.

By this arrangement, the swirl flow is formed in the medicine receiving chamber, and it is possible to discharge the powder medicine in the more diffuse state by the swirl flow, and to more certainly administer the powder medicine to the bottom of the nasal cavity. Accordingly, it is possible to restrict the powder medicine from remaining in the powder medicine administering device.

In the devices according to the embodiments of the present invention, the medicine carrying chamber is the recessed portion with the bottom portion.

By this arrangement, it is possible to further simplify the medicine carrying chamber. The sealing for preventing the leakage of the powder medicine and the air can be limited to the sliding surface located on the opening's side, between the main body and the movable member.

In the device according to the embodiments of the present invention, the medicine carrying chamber is the bottom recessed portion recessed in the curved form. The medicine discharge passage upstream of the medicine carrying chamber at the connection part with the medicine carrying chamber is directed to the recessed portion when the medicine carrying chamber is connected with the medicine discharge passage.

By this arrangement, it is possible to readily form the stirred flow of the powder medicine and the air along the curved recessed portion when the medicine carrying chamber is connected with the medicine discharge passage. Accordingly, it is possible to discharge the powder medicine in the more diffuse state, and to certainly administer the powder medicine to the bottom of the nasal cavity. Moreover, it is possible to restrict the powder medicine from remaining in the powder medicine administering device.

In the device according to the embodiments of the present invention, the air chamber within the air supply section is connected with the outside through the medicine discharge passage, irrespective of the position of the movable member.

By this arrangement, there is no need to consider the increase of the pressure in the air chamber by the pressing the pump member in the state in which the air chamber is enclosed in the sealed state. Accordingly, it is possible to reduce the rigidity and the strength of the pump member and so on, and to contribute to the size reduction and the weight reduction of the powder medicine administering device. Moreover, it is possible to omit the introduction valve for introducing the air to the air chamber.

In the device according to the embodiments of the present invention, below the inclined portion of the side wall surface, there is provided the portion which has the steeper gradient than the upper portion (the inclined portion).

By this arrangement, it is possible to vary the movement of the powder medicine within the powder medicine storage chamber by the variation in the gradient of the side wall surface, and to restrict the powder medicine from aggregating and adhering in the medicine storage chamber.

In the devices according to the embodiments of the present invention, the medicine carrying chamber is formed at a position eccentric to the center of the upper portion of the medicine storage chamber.

Accordingly, it is possible to restrict the powder medicine from moving uniformly within medicine storage chamber, and from aggregating and adhering in the medicine storage chamber.

This application is based on a prior Japanese Patent Application No. 2005-168681 filed on Jun. 8, 2005, and a prior Japanese Patent Application No. 2006-062700 filed on Mar. 8, 2006. The entire contents of these Japanese Patent Applications No. 2005-168681 and No. 2006-062700 are hereby incorporated by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. A powder medicine administering device comprising:

a main body;

an air supply section arranged to supply air under pressure; and a movable member rotatably attached to the main body, and arranged to be rotated relative to the main body from a first position through a second position to a third position, one of the main body and the movable member including a side wall portion defining a medicine storage chamber receiving a powder medicine in a substantially closed state, and including an opening closed by a sliding surface of the other of the main body and the movable member when the movable member is located at the second position, the side wall portion being inclined radially inward toward the opening near the opening of the medicine storage chamber, the one of the main body and the movable member being formed with a medicine discharge passage arranged to receive the supply of the air from the air supply section, and the other of the main body and the movable member being formed with a medicine carrying chamber arranged to be connected with the opening of the medicine storage chamber when the movable member is located at the first position, and arranged to be connected with the medicine discharge passage when the movable member is located at the third position, wherein the movable member rotates relative to the main body around a pivot, wherein the moveable member rotates around an axis which extends in a longitudinal direction of the powder medicine administering device, and wherein the pivot is provided at a distance from a center axis of the powder medicine administering device, thereby providing an offset of the moveable member from the main body when rotated into said third position.

2. The powder medicine administering device as claimed in claim 1, wherein the movable member is moved relative to the main body so that the movable member is projected with reference to an outside surface of the main body.

3. The powder medicine administering device as claimed in claim 1, wherein the main body is formed with the medicine storage chamber; and the movable member is formed with the medicine carrying chamber.

4. A powder medicine administering device comprising:

a main body;

an air supply section arranged to supply air under pressure; and a movable member slidably attached to the main body, and arranged to be moved relative to the main body from a first position through a second position to a third position, the device having a center axis that extends in a longitudinal direction with respect to the main body and the air supply section and the moveable member being rotatable around an axis which also extends in said longitudinal direction, is parallel thereto but is offset from said center axis;

the movable member including a side wall portion defining a medicine storage chamber receiving a powder medicine in a substantially closed state, and including an opening closed by a sliding surface of the main body when the movable member is located at the second position, the side wall portion being inclined radially inward toward the opening near the opening of the medicine storage chamber, the movable member being formed with a medicine discharge passage arranged to receive the supply of the air from the air supply section, and the main body including a medicine carrying chamber arranged to be connected with the opening of the medicine storage chamber when the movable member is located at the first position, and arranged to be connected with the medicine discharge passage when the movable member is located at the third position, wherein the medicine carrying chamber does not move relative to the air supply section when the movable member moves relative to the main body.

5. The powder medicine administering device as claimed in claim 1, wherein the movable member is moved from the first position through the second position to the third position so that the medicine carrying chamber supplies the powder medicine to the medicine discharge passage.

6. The powder medicine administering device as claimed in claim 5, wherein the powder medicine administering device further comprises a stirred flow forming section to stir the powder medicine in the medicine discharge passage, and the air supplied under the pressure by the air supply section.

7. The powder medicine administering device as claimed in claim 1, wherein the medicine carrying section serves as part of the stirred flow forming section when the medicine carrying chamber is connected with the medicine discharge passage.

8. The powder medicine administering device as claimed in claim 1, wherein the powder medicine administering device further comprises a medicine receiving chamber located under the medicine carrying chamber when the medicine carrying chamber is connected with the medicine discharge passage.

9. The powder medicine administering device as claimed in claim 1, wherein the medicine carrying chamber is a recessed portion including a bottom portion.

10. The powder medicine administering device as claimed in claim 1, wherein the movable member is a slider arranged to be moved in a direction substantially perpendicular to the axial direction; the medicine carrying chamber is a recessed portion including a bottom portion; and the recessed portion is opened in an upper surface of the slider.

11. The powder medicine administering device as claimed in claim 9, wherein the bottom portion of the recessed portion is curved; and the medicine discharge passage upstream of the recessed portion is directed to the bottom portion of the recessed portion when the medicine carrying chamber is connected with the medicine discharge passage.

12. The powder medicine administering device as claimed in claim 1, wherein the air supply section includes an air chamber; and the air chamber of the air supply section is connected through the medicine discharge passage to an outside, irrespective of the position of the movable member.

13. A powder medicine administering device as defined in claim 1, wherein the side wall portion is a first side wall portion;

wherein the powder medicine administering device further comprises a second side wall portion defining the medicine storage chamber, and being inclined radially inward toward the opening;

wherein the second side wall portion is located below the first side wall portion so that a lower edge of the first side wall portion is located above an upper edge of the second side wall portion in an axial direction of the opening;

wherein the second side wall portion has an inclination larger than an inclination of the first side wall portion, and wherein the lower edge of the first side wall portion contacts the upper edge of the second side wall portion.

14. The powder medicine administering device as claimed in claim 1, wherein the side wall portion is a first side wall portion; the powder medicine administering device further comprises a third side wall portion defining an upper portion of the medicine storage chamber, and extending in a substantially axial direction; and the medicine carrying chamber is located at a position eccentric to a center of an upper portion of the medicine storage chamber when the medicine carrying chamber is connected with the medicine storage chamber.

15. The powder medicine administering device as claimed in claim 1, wherein the medicine discharge passage includes a first medicine discharge passage upstream of the medicine carrying chamber, and a second medicine discharge passage downstream of the medicine carrying chamber; and the first medicine discharge passage extends in a direction crossing the second medicine discharge passage when the medicine carrying chamber is connected with the medicine discharge passage.

16. The powder medicine administering device as claimed in claim 1, wherein the other of the main body and the movable member is formed with the medicine discharge passage.

* * * * *